US012064399B2

(12) United States Patent
Guy et al.

(10) Patent No.: US 12,064,399 B2
(45) Date of Patent: *Aug. 20, 2024

(54) USE OF CANNABINOIDS IN THE TREATMENT OF EPILEPSY

(71) Applicant: Jazz Pharmaceuticals Research UK Limited, Kent (GB)

(72) Inventors: Geoffrey Guy, Cambridge (GB); Stephen Wright, Altrincham (GB); Orrin Devinsky, New York, NY (US)

(73) Assignee: Jazz Pharmaceuticals Research UK Limited, Kent (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/744,224

(22) Filed: May 13, 2022

(65) Prior Publication Data

US 2022/0387348 A1     Dec. 8, 2022

Related U.S. Application Data

(63) Continuation of application No. 16/893,018, filed on Jun. 4, 2020, now Pat. No. 11,357,741, which is a continuation of application No. 15/183,947, filed on Jun. 16, 2016, now Pat. No. 10,709,671.

(30) Foreign Application Priority Data

Jun. 17, 2015  (GB) ...................... 1510664

(51) Int. Cl.
| | |
|---|---|
| A61K 31/05 | (2006.01) |
| A61K 31/352 | (2006.01) |
| A61K 31/5513 | (2006.01) |
| A61K 36/185 | (2006.01) |
| A61K 45/06 | (2006.01) |
| A61K 47/10 | (2017.01) |
| A61K 47/26 | (2006.01) |
| A61K 47/44 | (2017.01) |
| A61P 25/08 | (2006.01) |

(52) U.S. Cl.
CPC ............ *A61K 31/05* (2013.01); *A61K 31/352* (2013.01); *A61K 31/5513* (2013.01); *A61K 36/185* (2013.01); *A61K 45/06* (2013.01); *A61K 47/10* (2013.01); *A61K 47/26* (2013.01); *A61K 47/44* (2013.01); *A61P 25/08* (2018.01)

(58) Field of Classification Search
CPC .. A61K 31/05; A61K 31/352; A61K 31/5513; A61K 36/185; A61K 45/06; A61K 47/10; A61K 47/26; A61K 47/44; A61P 25/08
See application file for complete search history.

(56) References Cited

U.S. PATENT DOCUMENTS

| | | |
|---|---|---|
| 2,304,669 A | 12/1942 | Adams |
| 6,383,513 B1 | 5/2002 | Watts et al. |
| 6,403,126 B1 | 6/2002 | Webster |
| 6,949,582 B1 | 9/2005 | Wallace |
| 7,025,992 B2 | 4/2006 | Whittle et al. |
| 8,222,292 B2 | 7/2012 | Goskonda et al. |
| 8,293,786 B2 | 10/2012 | Stinchcomb |
| 8,603,515 B2 | 12/2013 | Whittle |
| 8,632,825 B2 | 1/2014 | Velasco Diez et al. |
| 8,673,368 B2 | 3/2014 | Guy et al. |
| 8,790,719 B2 | 7/2014 | Parolaro et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,095,555 B2 | 8/2015 | Winnicki |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,477,019 B2 | 10/2016 | Li et al. |
| 9,492,438 B2 | 11/2016 | Pollard |
| 9,522,123 B2 | 12/2016 | Whalley et al. |
| 9,630,941 B2 | 4/2017 | Elsohly et al. |
| 9,675,654 B2 | 6/2017 | Parolaro et al. |
| 9,680,796 B2 | 6/2017 | Miller et al. |
| 9,730,911 B2 | 8/2017 | Verzura et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 9,962,341 B2 | 5/2018 | Stott et al. |
| 10,039,724 B2 | 8/2018 | Stott et al. |

(Continued)

FOREIGN PATENT DOCUMENTS

| | | |
|---|---|---|
| CA | 2737447 A1 | 10/2012 |
| CA | 2859934 A1 | 3/2016 |

(Continued)

OTHER PUBLICATIONS

Devinsky et al.(Year: 2014).*

(Continued)

*Primary Examiner* — Jeffrey S Lundgren
*Assistant Examiner* — Ibrahim D Bori
(74) *Attorney, Agent, or Firm* — COOLEY LLP

(57) ABSTRACT

The present invention relates to the use of cannabidiol (CBD) in the treatment of focal seizures. In one embodiment the patients suffering from focal seizures are children and young adults. CBD appears particularly effective in reducing focal seizures in patients suffering with etiologies that include: Lennox-Gastaut Syndrome; Tuberous Sclerosis Complex; Dravet Syndrome; CDKL5; Neuronal ceroid lipofuscinoses (NCL); febrile infection related epilepsy syndrome (FIRES); Aicardi syndrome and brain abnormalities in comparison to other seizure types. Significantly CBD additionally is very effective in the reduction of a sub-type of focal seizures, focal seizures with impairment.

28 Claims, 1 Drawing Sheet

(56) References Cited

U.S. PATENT DOCUMENTS

| | | |
|---|---|---|
| 10,092,525 B2 | 10/2018 | Guy et al. |
| 10,098,867 B2 | 10/2018 | Javid et al. |
| 10,111,840 B2 | 10/2018 | Guy et al. |
| 10,137,095 B2 | 11/2018 | Guy et al. |
| 10,220,005 B2 | 3/2019 | Martinez-Orgado |
| 10,226,433 B2 | 3/2019 | DiMarzo et al. |
| 10,583,096 B2 | 3/2020 | Guy et al. |
| 10,603,288 B2 | 3/2020 | Guy et al. |
| 10,653,641 B2 | 5/2020 | Robson et al. |
| 10,709,671 B2 | 7/2020 | Guy et al. |
| 10,709,673 B2 | 7/2020 | Guy et al. |
| 10,709,674 B2 | 7/2020 | Guy et al. |
| 10,729,665 B2 | 8/2020 | Whalley et al. |
| 10,758,514 B2 | 9/2020 | Liu et al. |
| 10,765,643 B2 | 9/2020 | Guy et al. |
| 10,799,467 B2 | 10/2020 | Whalley et al. |
| 10,807,777 B2 | 10/2020 | Whittle |
| 10,849,860 B2 | 12/2020 | Guy et al. |
| 10,918,608 B2 | 2/2021 | Guy et al. |
| 10,925,525 B2 | 2/2021 | Nakaji |
| 10,966,939 B2 | 4/2021 | Guy et al. |
| 11,000,486 B2 | 5/2021 | Liu et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Guy et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,224,600 B2 | 1/2022 | Vangara et al. |
| 11,229,612 B2 | 1/2022 | Wright et al. |
| 11,291,631 B2 | 4/2022 | Shah |
| 11,311,498 B2 | 4/2022 | Guy et al. |
| 11,318,109 B2 | 5/2022 | Whalley et al. |
| 11,331,279 B2 | 5/2022 | Vangara et al. |
| 11,357,741 B2 | 6/2022 | Guy et al. |
| 11,400,055 B2 | 8/2022 | Guy et al. |
| 11,406,623 B2 | 8/2022 | Guy et al. |
| 11,413,266 B2 | 8/2022 | Biro et al. |
| 11,419,829 B2 | 8/2022 | Whalley et al. |
| 11,426,362 B2 | 8/2022 | Wright et al. |
| 11,446,258 B2 | 9/2022 | Guy et al. |
| 11,590,087 B2 | 2/2023 | Guy et al. |
| 11,633,369 B2 | 4/2023 | Guy et al. |
| 11,679,087 B2 | 6/2023 | Guy et al. |
| 11,684,598 B2 | 6/2023 | Stott et al. |
| 11,701,330 B2 | 7/2023 | Guy et al. |
| 11,709,671 B2 | 7/2023 | Joubert et al. |
| 11,766,411 B2 | 9/2023 | Guy et al. |
| 11,793,770 B2 | 10/2023 | Stott et al. |
| 11,806,319 B2 | 11/2023 | Wilkhu et al. |
| 11,865,102 B2 | 1/2024 | Guy et al. |
| 2004/0034108 A1 | 2/2004 | Whittle |
| 2004/0049059 A1 | 3/2004 | Mueller |
| 2004/0110828 A1 | 6/2004 | Chowdhury et al. |
| 2004/0147767 A1 | 7/2004 | Whittle et al. |
| 2005/0042172 A1 | 2/2005 | Whittle |
| 2005/0266108 A1 | 12/2005 | Flockhart et al. |
| 2006/0039959 A1 | 2/2006 | Wessling |
| 2006/0167283 A1 | 7/2006 | Flockhart et al. |
| 2007/0060638 A1 | 3/2007 | Olmstead |
| 2007/0099987 A1 | 5/2007 | Weiss et al. |
| 2007/0238786 A1 | 10/2007 | Hobden et al. |
| 2008/0112895 A1 | 5/2008 | Kottayil et al. |
| 2008/0119544 A1 | 5/2008 | Guy et al. |
| 2008/0188461 A1 | 8/2008 | Guan |
| 2009/0036523 A1 | 2/2009 | Stinchcomb et al. |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0273895 A1 | 10/2010 | Stinchcomb et al. |
| 2010/0317729 A1 | 12/2010 | Guy et al. |
| 2011/0028431 A1 | 2/2011 | Zerbe et al. |
| 2011/0033529 A1 | 2/2011 | Samantaray et al. |
| 2011/0038958 A1 | 2/2011 | Kikuchi et al. |
| 2011/0082195 A1 | 2/2011 | Guy et al. |
| 2011/0150825 A1 | 6/2011 | Buggy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0270845 A1 | 10/2012 | Bannister |
| 2013/0143894 A1 | 6/2013 | Bergstrom et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0342902 A1 | 12/2015 | Vangara et al. |
| 2015/0343071 A1 | 12/2015 | Vangara et al. |
| 2015/0359755 A1 | 12/2015 | Guy et al. |
| 2015/0359756 A1 | 12/2015 | Guy et al. |
| 2016/0010126 A1 | 1/2016 | Poulos et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2016/0317468 A1 | 11/2016 | Sankar et al. |
| 2016/0338974 A1 | 11/2016 | Aung-Din |
| 2017/0007551 A1 | 1/2017 | Guy et al. |
| 2017/0008868 A1 | 1/2017 | Dialer et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0224634 A1 | 8/2017 | Vangara et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Wilkhu et al. |
| 2018/0028489 A1 | 2/2018 | Vangara et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0031601 A1 | 1/2019 | Elsohly et al. |
| 2019/0083418 A1 | 3/2019 | Guy et al. |
| 2019/0091171 A1 | 3/2019 | Guy et al. |
| 2019/0160393 A1 | 5/2019 | Marshall et al. |
| 2019/0167583 A1 | 6/2019 | Shah |
| 2019/0175547 A1 | 6/2019 | Stott et al. |
| 2019/0247324 A1 | 8/2019 | Whalley et al. |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0000741 A1 | 1/2020 | Guy et al. |
| 2020/0069608 A1 | 3/2020 | Guy et al. |
| 2020/0138738 A1 | 5/2020 | Guy et al. |
| 2020/0179303 A1 | 6/2020 | Guy et al. |
| 2020/0206152 A1 | 7/2020 | Stott et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0323792 A1 | 10/2020 | Guy et al. |
| 2020/0352878 A1 | 11/2020 | Guy et al. |
| 2020/0368179 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |

(56) References Cited

U.S. PATENT DOCUMENTS

| | | |
|---|---|---|
| 2021/0069333 A1 | 3/2021 | Velasco Diez et al. |
| 2021/0093581 A1 | 4/2021 | Guy et al. |
| 2021/0100755 A1 | 4/2021 | Whalley et al. |
| 2021/0145765 A1 | 5/2021 | Guy et al. |
| 2021/0169824 A1 | 6/2021 | Guy et al. |
| 2021/0177773 A1 | 6/2021 | Guy et al. |
| 2021/0196651 A1 | 7/2021 | Guy et al. |
| 2021/0230145 A1 | 7/2021 | Blankman et al. |
| 2021/0244685 A1 | 8/2021 | Guy et al. |
| 2021/0167950 A1 | 9/2021 | Guy et al. |
| 2021/0290565 A1 | 9/2021 | Guy et al. |
| 2021/0308072 A1 | 10/2021 | Wright et al. |
| 2021/0330636 A1 | 10/2021 | Guy et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0087951 A1 | 3/2022 | Guy et al. |
| 2022/0096397 A1 | 3/2022 | Wright et al. |
| 2022/0168266 A1 | 6/2022 | Guy et al. |
| 2022/0183997 A1 | 6/2022 | Guy et al. |
| 2022/0184000 A1 | 6/2022 | Guy et al. |
| 2022/0202738 A1 | 6/2022 | Guy et al. |
| 2022/0211629 A1 | 7/2022 | Wilkhu et al. |
| 2022/0226257 A1 | 7/2022 | Guy et al. |
| 2022/0233495 A1 | 7/2022 | Silcock et al. |
| 2022/0249396 A1 | 8/2022 | Guy et al. |
| 2022/0257529 A1 | 8/2022 | Guy et al. |
| 2022/0265573 A1 | 8/2022 | Guy et al. |
| 2022/0288055 A1 | 9/2022 | Silcock et al. |
| 2022/0323375 A1 | 10/2022 | Guy et al. |
| 2022/0378714 A1 | 12/2022 | Guy et al. |
| 2022/0378715 A1 | 12/2022 | Guy et al. |
| 2022/0378717 A1 | 12/2022 | Guy et al. |
| 2022/0378738 A1 | 12/2022 | Guy et al. |
| 2022/0387347 A1 | 12/2022 | Whalley et al. |
| 2022/0395470 A1 | 12/2022 | Whalley et al. |
| 2022/0395471 A1 | 12/2022 | Guy et al. |
| 2023/0000789 A1 | 1/2023 | Guy et al. |
| 2023/0022487 A1 | 1/2023 | Guy et al. |
| 2023/0024312 A1 | 1/2023 | Whalley et al. |
| 2023/0026079 A1 | 1/2023 | Guy et al. |
| 2023/0032502 A1 | 2/2023 | Guy et al. |
| 2023/0038423 A1 | 2/2023 | Silcock et al. |
| 2023/0068885 A1 | 3/2023 | Guy et al. |
| 2023/0143812 A1 | 5/2023 | Knappertz et al. |
| 2023/0235825 A1 | 7/2023 | Thompson et al. |
| 2023/0248664 A1 | 8/2023 | Guy et al. |
| 2023/0263744 A1 | 8/2023 | Guy et al. |
| 2023/0277560 A1 | 9/2023 | Checketts et al. |
| 2023/0277562 A1 | 9/2023 | Checketts et al. |
| 2023/0277563 A1 | 9/2023 | Checketts et al. |
| 2023/0285420 A1 | 9/2023 | Checketts et al. |
| 2023/0285421 A1 | 9/2023 | Checketts et al. |
| 2023/0285423 A1 | 9/2023 | Checketts et al. |
| 2023/0285424 A1 | 9/2023 | Checketts et al. |
| 2023/0285427 A1 | 9/2023 | Checketts et al. |
| 2023/0301934 A1 | 9/2023 | Whalley et al. |
| 2023/0301936 A1 | 9/2023 | Guy et al. |
| 2023/0310464 A1 | 10/2023 | Checketts et al. |
| 2023/0346809 A1 | 11/2023 | Craig et al. |
| 2023/0372367 A1 | 11/2023 | Checketts et al. |
| 2023/0372368 A1 | 11/2023 | Checketts et al. |
| 2024/0016819 A1 | 1/2024 | Craig et al. |
| 2024/0025858 A1 | 1/2024 | Silcock et al. |
| 2024/0033229 A1 | 2/2024 | Guy et al. |
| 2024/0043388 A1 | 2/2024 | Silcock et al. |
| 2024/0050452 A1 | 2/2024 | Craig et al. |

FOREIGN PATENT DOCUMENTS

| | | |
|---|---|---|
| CN | 101040855 A | 9/2007 |
| CN | 103110582 A | 5/2013 |
| CN | 104490873 A | 4/2015 |
| CN | 108 236 608 A | 7/2018 |
| CN | 110 215 443 A | 9/2019 |
| CN | 110 279 617 A | 9/2019 |
| DE | 10 2012 105 063 A1 | 12/2013 |
| EP | 2 311 475 A2 | 4/2011 |
| EP | 2 448 637 B1 | 5/2012 |
| EP | 2 578 561 A1 | 4/2013 |
| EP | 3 157 512 B1 | 5/2018 |
| GB | 2002754 A | 2/1979 |
| GB | 2 377 633 A | 1/2003 |
| GB | 2 380 129 A | 4/2003 |
| GB | 2 381 194 A | 4/2003 |
| GB | 2384707 A | 8/2003 |
| GB | 2434097 A | 7/2007 |
| GB | 2434312 A | 7/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2 485 291 A | 5/2012 |
| GB | 2 487 183 A | 7/2012 |
| GB | 2471565 B | 7/2012 |
| GB | 2478072 B | 12/2012 |
| GB | 2478074 B | 12/2012 |
| GB | 2492487 A | 1/2013 |
| GB | 2487712 A | 10/2015 |
| GB | 2 530 001 A | 3/2016 |
| GB | 2531093 A | 4/2016 |
| GB | 2531278 A | 4/2016 |
| GB | 2531281 A | 4/2016 |
| GB | 2531282 A | 4/2016 |
| GB | 2539472 A | 12/2016 |
| GB | 2 542 155 A | 3/2017 |
| GB | 2438682 A | 12/2017 |
| GB | 2551987 A | 1/2018 |
| GB | 2584 140 A | 11/2020 |
| WO | WO 01/95899 A2 | 12/2001 |
| WO | WO 2002/064109 A2 | 8/2002 |
| WO | WO 02/089945 A2 | 11/2002 |
| WO | WO 2003/099302 A1 | 12/2003 |
| WO | WO 2004/016246 A1 | 2/2004 |
| WO | WO 2004/016277 A2 | 2/2004 |
| WO | WO 2004/026802 A1 | 4/2004 |
| WO | WO 2005/120478 A1 | 12/2005 |
| WO | WO 2006/054057 A2 | 5/2006 |
| WO | WO 2006/017892 A1 | 12/2006 |
| WO | WO 2006/133941 A2 | 12/2006 |
| WO | WO 2007/032962 A2 | 3/2007 |
| WO | WO 2007/052013 A1 | 5/2007 |
| WO | WO 2007/083098 A1 | 7/2007 |
| WO | WO 2007/138322 A1 | 12/2007 |
| WO | WO 2008/019146 A2 | 2/2008 |
| WO | WO 2008/094181 A3 | 8/2008 |
| WO | WO 2008/129258 A1 | 10/2008 |
| WO | WO 2008/144475 A1 | 11/2008 |
| WO | WO 2008/021394 A2 | 12/2008 |
| WO | WO 2008/146006 A1 | 12/2008 |
| WO | WO 2009/007697 A1 | 1/2009 |
| WO | WO 2009/007698 A1 | 1/2009 |
| WO | WO 2009/020666 A1 | 2/2009 |
| WO | WO 2009/093018 A1 | 7/2009 |
| WO | WO 2010/012506 A1 | 2/2010 |
| WO | WO 2011/001169 A1 | 1/2011 |
| WO | WO 2011/121351 A1 | 10/2011 |
| WO | WO 2012/033478 A1 | 3/2012 |
| WO | WO 2012/093255 A1 | 7/2012 |
| WO | WO 2012/160358 A1 | 11/2012 |
| WO | WO 2013/032351 A1 | 3/2013 |
| WO | WO 2013/045891 A1 | 4/2013 |
| WO | WO 2014/168131 A1 | 11/2013 |
| WO | WO 2014/108899 A1 | 7/2014 |
| WO | WO 2014/146699 A1 | 9/2014 |
| WO | WO 2015/065544 A1 | 5/2015 |

(56) References Cited

FOREIGN PATENT DOCUMENTS

| | | |
|---|---|---|
| WO | WO 2015/142501 A1 | 9/2015 |
| WO | WO 2015/184127 A2 | 12/2015 |
| WO | WO 2015/193667 A1 | 12/2015 |
| WO | WO 2015/193668 A1 | 12/2015 |
| WO | WO 2016/059399 A1 | 4/2016 |
| WO | WO 2016/059403 A1 | 4/2016 |
| WO | WO 2016/059405 A1 | 4/2016 |
| WO | WO 2016/084075 A1 | 6/2016 |
| WO | WO 2015/187988 A1 | 7/2016 |
| WO | WO 2016/118391 A1 | 7/2016 |
| WO | WO 2016/147186 A1 | 9/2016 |
| WO | WO 2016/022936 A1 | 11/2016 |
| WO | WO 2016/176279 A1 | 11/2016 |
| WO | WO 2016/191651 A1 | 12/2016 |
| WO | WO 2016/199148 A1 | 12/2016 |
| WO | WO 2016/203239 A1 | 12/2016 |
| WO | WO 2017/042567 A1 | 3/2017 |
| WO | WO 2017/139496 A1 | 8/2017 |
| WO | WO 2017/168138 A1 | 10/2017 |
| WO | WO 2017/203529 A1 | 11/2017 |
| WO | WO 2017/204986 A1 | 11/2017 |
| WO | WO 2018/002636 A1 | 1/2018 |
| WO | WO 2018/002637 A1 | 1/2018 |
| WO | WO 2018/002665 A1 | 1/2018 |
| WO | WO 2018/011808 A1 | 1/2018 |
| WO | WO 2018/037203 A1 | 3/2018 |
| WO | WO 2018/115962 A1 | 6/2018 |
| WO | WO 2018/200024 A1 | 11/2018 |
| WO | WO 2018/234811 A1 | 12/2018 |
| WO | WO 2019/020738 A1 | 1/2019 |
| WO | WO 2019/097238 A1 | 5/2019 |
| WO | WO 2019/207319 A1 | 10/2019 |
| WO | WO 2019/210210 A1 | 10/2019 |
| WO | WO 2019/211795 A1 | 11/2019 |
| WO | WO 2020/234569 A1 | 11/2020 |

OTHER PUBLICATIONS

Adams, R. et al., "Isolation of Cannabinol, Cannabidiol and Quebrachitol from Red Oil of Minnesota Wild Hemp," J. Am. Chem. Soc. 1940, 62, 8, 2194-2196.

Akiyama, M. et al., "Dravet Syndrome:A Genetic Epileptic Disorder," Acta. Med. Okayama, 66(5):369-376 (2012).

Approval Letter for NDA 210365 Epidiolex, Jun. 25, 2018, 12 pages.

Arzimanoglou et al., "All children who experience epileptic falls do not necessarily have Lennox-Gastaut syndrome . . . but many do," Epileptic Disord. 2011, 13: S3-S13 (2011).

[No Author Listed], "High Rollers Bet on Cannabidiol (CBD)—Medical Marijuana Patients Come Up Short," Mar. 3, 2013, 9 pages; https://www.420magazine.com/community/threads/high-rollers-bet-on-cannabidiol-cbd-%E2%80%94-medical-marijuana-patients-come-up-short.185325/.

[No Author Listed], "Selected Media Examples of Pediatric Applications OfCannabidiol (CBD)," Jun. 30, 2013, 4 pages; https://www.420magazine.com/community/threads/selected-media-examples-of-pediatric-applications-of-cannabidiol-cbd.192155/.

Allen G., "Florida Bill Would Allow Medical Marijuana for Child Seizures," Jan. 16, 2014, retrieved from https://www.npr.org/sections/health-shots/2014/01/16/262481852/florida-bill-would-allow-marijuana-extract-for-child-seizures, 16 pages.

Amada, N. et al., "Cannabidivarin (CBDV) suppresses pentylenetetrazole (PTZ)-induced increases in epilepsy-related gene expression," 2013, PeerJ, 1:e214; 18 pages; http://dx.doi.org/10.7717/peerj.214.

Bell, J., "Treatment With CBD in Oily Solution of Drug-Resistant Paediatric Epilepsies," Oct. 18, 2011, 3 pages; https://www.420magazine.com/community/threads/treatment-with-cbd-in-oily-solution-of-drug-resistant-paediatric-epilepsies.154896/.

Bergamaschi, M. M. et al., "Safety and Side Effects of Cannabidiol, a Cannabis sativa Constituent," Current Drug Safety, 6:237-249 (2011).

Bienenstock, D., "A Comprehensive History of Marijuana's Epilepsy-Treating Compound, CBD," Jun. 2014, Vice Article, retrieved from https://www.vice.com/da/article/mv53yp/desperately-seeking-cbd, 17 pages.

Carlini, E. A. et al., "Letter: Cannabidiol and Cannabis sativa extract protect mice and rats against convulsive agents," J Pharm Pharmacol. Aug. 1973;25(8):664-5. doi: 10.1111/j.2042-7158.1973.tb10660.x.

Carvill, G. L. et al., "GABRA1 and STXBP1: Novel generic causes of Dravet Syndrome," Neurology, 82:1245-1253 (2014).

Chiron, S., "Stiripentol for the treatment of Dravet syndrome," Orphan Drugs: Research and Reviews, 4:29-38 (2014).

Chu-Shore, C. J. et al., "The natural history of epilepsy in tuberous sclerosis complex," Epilepsia, 51(7): 1236-1241, 2010; doi: 10.1111/j.1528-1167.2009.02474.

Cilio, M. R. et al., "The case for assessing cannabidiol | epilepsy," Epilepsia, 55(6):787-790 (2014).

clinical trials.gov [online], Identifier: NCT02224690, a Study to Investigate the Efficacy and Safety of Cannabidiol (GWP42003-P; CBD) as Adjunctive Treatment for Seizures Associated With Lennox-Gastaut Syndrome in Children and Adults (GWPCARE4) Jazz Pharmaceuticals, U.S. National Library of Medicine, last update posted Sep. 8, 2022, 3 pages; Retrieved from https://clinicaltrials.gov/ct2/show/NCT02224690.

clinical trials.gov [online], Identifier: NCT02091206, a Dose Ranging Pharmacokinetics and Safety Study of GWP42003-P in Children With Dravet Syndrome (GWPCARE1), Jazz Pharmaceuticals, U.S. National Library of Medicine, last update posted Sep. 28, 2022, 9 pages; Retrieved from https://clinicaltrials.gov/ct2/show/NCT02091206.

clinical trials.gov [online], Identifier: NCT02006628, a study to compare the change in symptom severity in participants with schizophrenia or related psychotic disorderwhen treated with GWP42003 or placebo in conjunction with existing anti-psychotic therapy over a period of six weeks, Jazz Pharmaceuticals, U.S. National Library of Medicine, last update posted Sep. 28, 2022, 9 pages; Retrieved from https://clinicaltrials.gov/ct2/show/NCT02006628.

clinical trials.gov [online], Identifier: NCT02091375, Antiepileptic Efficacy Study of GWP42003-P in Children and Young Adults WithDravet Syndrome (GWPCARE1), Jazz Pharmaceuticals, U.S. National Library of Medicine, last update posted Sep. 28, 2022, 40 pages; Retrieved from https://www.clinicaltrials.gov/ct2/show/NCT02091375.

Collins, T. R., Collins TR. What Neurologists are Doing About Medical Marijuana?, Neurology Today, Apr. 17, 2014, vol. 4, issue 8, 8 pages.

Cotter, B., "Medicinal marijuana stops seizures, brings hope to little girl," The Gazette, Jun. 9, 2013, 8 pages; https://gazette.com/health/medicinal-marijuana-stops-seizures-brings-hope-to-a-little-girl/article_520b074e-5c46-5d75-af95-bdd060f4a8b9.html.

Cotterell, A., "How One Young Girl Could Change Idaho's Strict Marijuana Laws," Jun. 17, 2014; https://www.knkx.org/law/2014-06-19/how-one-young-girl-could-change-idahos-strict-marijuana-laws, 8 pages.

Crumrine, P. K., "Management of Seizures in Lennox-Gastaut Syndrome," Pediatr Drugs, 13(2):107-118 (2011).

Curatolo, P. et al., "Management of epilepsy associated with tuberous sclerosis complex (TSC): Clinical recommendations," European Journal of Paediatric Neurology, 16:582-586 (2012).

Depakene (valproic acid) capsules and oral solution, CV, Prescribing Information, 1978, 54 pages; https://www.accessdata.fda.gov/drugsatfda_docs/label/2013/018081s056lbl.pdf.

Diacomit™ Product Monograph, Submission Control 142417, Date of Preparation, Dec. 19, 2012, 37 pages.

Dilantin-125®, NDA 08762 Dilantin-125 (Phenytoin Oral Suspension, USP) FDA Approved Labeling Text dated Feb. 2013, 15 pages.

DiMarzo, V., Declaration Under 37 C.F.R. 1.132, dated Aug. 24, 2017, 21 pages.

Epilepsy Patients Flock to Colorado after Medical Pot Gives Them Hope, Nov. 18, 2013, CBS Colorado News, 4 pages.

Elsohly, M. & Gul, W., "Chemical constituents of marijuana: The complex mixture of natural cannabinoids," Life Sciences, 78:539-548 (2005).

(56) References Cited

OTHER PUBLICATIONS

FDA'S Guidance for Industry Q3A Impurities in New Drug Substances, Revision 2, Jun. 2008, 17 pages.
FDA Guideline for Submitting Supporting Documentation in Drug Applications for the Manufacture of Drug Substances, published in 1987, 20 pages.
Fernandez-Ruiz, J et al., "Cannabidiol for neurodegenerative disorders: important new clinical applications for this phytocannabinoid?" British Journal of Pharmacology, 75(2):323-333 (2012).
Flatow, N., "How Medical Marijuana Is Giving a Six-Year-Old Boy New Life," Sep. 18, 2012, 2 pages; https://archive.thinkprogress.org/how-medical-marijuana-is-giving-a-six-year-old-boy-new-life-b5a486fb1d48/.
Gaoni, Y. & Mechoulam, R., "The Isolation and Structure of A1-Tetrahydrocannabinol and Other Neutral Cannabinoids from Hashish," J Am Chem Soc. Jan. 1, 19713;93(1):217-24. doi: 10.1021/ja00730a036.
Gaoni, Y. & Mechoulam, R., "Isolation, Structure, and Partial Synthesis of an Active Constituent of Hashish," J. Am. Chem. Soc. 1964, 86, 8, 1646-1647.
Garde, D., "GW Pharmaceuticals Announces Physician Reports of Epidiolex Treatment Effect in Children and Young Adults With Treatment-Resistant Epilepsy From Physician-Led Expanded Access Treatment Program," Jun. 17, 2014, 4 pages; https://www.fiercebiotech.com/biotech/gw-pharmaceuticals-announces-physician-reports-of-epidiolex-r-treatment-effect-children-and.
Gedde et al., "3.330 Whole Cannabis Extract of High Concentration Cannaboidol May Calm Seizures in Highly Refractory Pediatric Epilepsies," American Epilepsy Society, Dec. 2013, pp. 449-1450.
Geffrey, A. et al., "Cannabidiol (CBD) Treatment for Refractory Epilepsy in Tuberous Sclerosis Complex (TSC)," Dec. 4, 2014; www.aesnet.org, Abstract 2.427, 2 pages.
Gloss, D. & Vickrey, B., "Cannabinoids for epilepsy (Review)," Cochrane Database of Systematic Reviews 2014, Issue 3. Art. No. CD009270, 9 pages; DOI: 10.1002/14651858.CD009270.pub3.
Haller, S. & Carroll, I., "Medical marijuana for kids? Some praise results while others worry about risks," Jul. 9, 2013, 3 pages; https://www.nbcnews.com/healthmain/medical-marijuana-kids-some-praise-results-while-others-worry-about-6c10506407.
Hanus et al., "Phyto-cannabinoids: a unified critical inventory," Review Article, Natural Product Reports; Royal Society of Chemistry, vol. 33, No. 12, Dec. 2016, pp. 1347, 1448, 37 pages.
Hefler, J., "Parents of epileptic N.J. tot lament medical marijuana delays," The Philadelphia Enquirer, Jun. 22, 2013, 5 pages; https://www.inquirer.com/philly/health/20130623_Parents_of_epileptic_N_J_tot_lament_medical_marijuana_delays.html.
Hegde, M. et al., "Seizure exacerbation in two patients with focal epilepsy following marijuana cessation," Epilepsy & Behavior, 25:563-566 (2012).
Hill et al., "Cannabidivarin is anticonvulsant in mouse and rat," Br. J Pharmacol, 167(8):1629-1642 (2012).
Hill, A. J. et al., "Phytocannabinoids as novel therapeutic agents in CNS disorders," Pharmacology & Therapeutics, 133:79-97 (2012).
Hillig, K. W. & Mahlberg, P. G., "A chemotaxonomic analysis of cannabinoid variation in Cannabis (Cannabaceae)," American Journal of Botany, 91(6):966-975 (2004).
Holmes, G. L. et al., "Tuberous Sclerosis Complex and Epilepsy: Recent Developments and Future Challenges," Epilepsia, 48(4):617-630, 2007.
Jacobson, C., "Treating Epilepsy with Pharmaceutical-Grade CBD", Cannabis Science Today, Podcast, 2023, transcript timeline 4 pages; https://agriculturalgenomics.org/podcast/season1/treating-epilepsy-with-pharmaceutical-grade-cbd/.
Jiang, R. et al., "Cannabidiol Is a Potent Inhibitor of the Catalytic Activity of Cytochrome P450 2C19," Drug Metab. Pharmacokinet., 28(4):332-338 (2013).
Jones, N. A. et al., "Cannabidiol exerts anti-convulsant effects in animal models of temporal lobe and partial seizures," Seizure, 21:344-352 (2012).

Jones, P. G. et al., "Cannabidiol," Acta Cryst., B33:3211-3214 (1977).
Kalepu, S. et al., "Oral lipid-based drug delivery systems—an overview," Acta Pharmaceutica Sinica B., 3(6):361-372 (2013).
Kassai et al., "Severe Myoclonic epilepsy in Infancy: A Systematic Review and a Meta-Analysis of Individual Patient Data," Epilepsia, 49(2):343-348 (2008).
Kerr, D. N. S. & Pillai, P. M., "Clobazam as adjunctive treatment in refractory epilepsy," British Medical Journal, 286:1246-1247 (1983).
Kopka, M., "Cannabinoids in the treatment of epilepsy—an updated review," Journal of Epileptology, 2019, 27:35-42; 10.21307/jepil-2019-004.
Krasowski, M. D., "Antiepileptic Drugs. Therapeutic Drug Monitoring of the Newer Generation Drugs," Jun. 2013, Clinical Laboratory News, https://www.aacc.org/cln/articles/2013/june/antiepileptic-drugs, 6 pages.
Leahy, J. T. et al., "Clobazam as an adjunctive therapy in treating seizures associated with Lennox-Gastaut syndrome," Neuropsychiatric Disease and Treatment, 7:673-681 (2011).
Leonard, B. E., "Therapeutic Uses of Cannabis," British Medical Association (BMA). Harwood Academic Publishers, UK. 1997, p. 592.
Loscher, W. & Rogawski, M. A., "How theories evolved concerning the mechanism of action of barbiturates," Epilepsia, 53(Suppl. 8):12-25, 2012; doi: 10.1111/epi.12025.
Marks, W. J. et al., "Management of Seizures and Epilepsy," Am Fam Physician. 1998;57(7):1589-1600.
Marinol® Product Description, NDA 18-651/S-025 and S-026, Jul. 2006, pp. 3-13.
Masangkay, E. G., "FDA Confirms GW Pharmaceuticals' IND for Epidiolex Trial in Dravet Syndrome," May 9, 2014, 2 pages.
Mechoulam, R. et al., "Cannabidiol—Recent Advances," Chemistry & Biodiversity, vol. 4, pp. 1678-1692 (2007).
Mechoulam, R., "Conversation with Ralph Mechoulam," Addiction Jun. 2007; 102(6):887-93. doi: 10.1111/j.1360-0443.2007.01795.x.
Mechoulam, R. & Parker, L. A., "The Endocannabinoid System and the Brain," Annu. Rev. Psychol. 2013. 64:21-47.
Mechoulam, R. & Parker, L. A., "Towards a better cannabis drug," British Journal of Pharmacology (2013) 170 1363-1364.
Moore, Y. et al., "Cannabidiol reduced frequency of convulsive seizures in drug resistant Dravet Syndrome," Structured Abstracts of Sentinel Articles: Picket, first published Sep. 22, 2017, reported in Arch Dis Child Educ Pract Ed Oct. 2018, vol. 103, No. 5., 2 pages. Abstract.
New Drug Application No. 210365 for Epidiolex (cannabidiol) 100 mg/ml oral solution, Jun. 25, 2018, 12 pages.
[No Author Listed], The Reuters Staff, BRIEF-GW Pharma receives FDA fast-track designation for Dravet syndrome treatment, Jun. 6, 2014, 1 page; https://www.reuters.com/article/gwpharmaceuticals-brief/brief-gw-pharma-receives-fda-fast-track-designation-for-dravet-syndrome-treatment-idUSFWN0OL01D20140606.
[No Author Listed], "Medical Cannabis Community Wants to Remain Apart," Medical Marijuana News, Apr. 3, 2013, 3 pages; Kitsap Peninsula Business Journal, available at: https://www.420magazine.com/community/threads/medical-cannabis-community-wants-to-remain-apart.186955/.
[No Author Listed], "Medical Marijuana for N.J. Children? It's All in Gov. Christie's Hands," CBS News New York, Jun. 27, 2013, 3 pages; https://www.cbsnews.com/newyork/news/medical-marijuana-for-n-j-children-its-all-in-gov-christies-hands/.
Onfi™ (clobazam) tablets Prescribing Information, NDA 202067 Onfi (clobazam) Tablets for oral use FDA Approved Labeling Text, dated Oct. 21, 2011, 28 pages.
Oguni, H. et al., "Long-Term Prognosis of Lennox-Gastaut Syndrome," Epilepsia, 37(Suppl 3):44-47 (1996).
Oguni, H. et al., "Severe myoclonic epilepsy in infants—a review based on the Tokyo women's Medical University series of 84 cases," Brain Dev., 23:736-748 (2010).
Panikasiwill, D. et al., "An endogenous cannabinoid (2-AG) is neuroprotective after brain injury," Nature 413:527-531 (2001).
Pellicia, et al.. International Association for Cannabis as Medicine, IACM 3rd Conference on Cannabinoids in Medicine, Sep. 9-10, 2005, 2005 Conference on Cannabinoids in Medicine, 72 pages.

(56) References Cited

OTHER PUBLICATIONS

Potter, C., "Cannabis Extract Brings Hope for Children with Epilepsy," Dec. 3, 2013, 3 pages.
"Pot or not? Why parents of kids with epilepsy want access to marijuana treatment," CTVNews.ca Staff, Published Thursday, Jul. 18, 2013; Last Updated Thursday, Jul. 18, 2013, 2 pages; https://www.ctvnews.ca/health/health-headlines/pot-or-not-why-parents-of-kids-with-epilepsy-want-access-to-marijuana-treatment-1.1372695?cache=.
Purcarin, G. & Ng, Y-T., "Experience in the use of clobazam in the treatment of Lennox-Gastaut syndrome," Ther Adv Neurol Disord 2014, vol. 7(3):169-176.
Ragona, F. et al., "Dravet syndrome: early clinical manifestations and cognitive outcome in 37 Italian patients," Brain Dev., 32:71-77 (2010).
Rowe, R. C. et al., "Handbook of Pharmaceutical Excipients," Pharmaceutical Press and American Pharmacists Association 2009, pp. 17-19; https://www.academia.edu/16731682/Handbook_of_Pharmaceutical_Excipients_6th_Edition.
Saade, D. & Joshi, C., "Pure Cannabidiol in the Treatment of Malignant Migrating Partial Seizures in Infancy: A Case Report," Pediatric Neurology, 52:544-547 (2015); http://dx.doi.org/10.1016/j.pediatrneurol.2015.02.008.
Schafroth, M. A. et al., "Stereodivergent Total Synthesis of $\Delta$9-Tetrahydrocannabinols," Angew. Chem. Int. Ed., 53:13898-13901 (2014).
Scheffer, I. E., "Diagnosis and long-term course of Dravet syndrome," Eur J of Paediatric Neurology 16 (2012) S5-S8.
Silva, R. et al., "Clobazam as Add-on Therapy in Children with Epileptic Encephalopathy," Can. J. Neurol. Sci., 33:209-213 (2006).
Smith, R. M. & Kempfert, K. D., "$\Delta$1-3,4-CIS-Tetrahydrocannabinol in Cannabis Sativa," Phytochemistry, 16:1088-1089 (1977).
Specchio, L. M. & Beghi, E., "Should Antiepileptic Drugs Be Withdrawn in Seizure-Free Patients?" CNS Drugs, 18(4):201-212 (2004).
Stewart, K., "Families migrating to Colorado for a medical marijuana miracle," Nov. 11, 2013, 8 pages; https://archive.sltrib.com/article.php?id=57052556&itype=CMSID.
Stinchcomb, A. L. et al., "Human skin permeation of $\Delta$8-tetrahydrocannabinol, cannabidiol and cannabinol," JPP 2004, 56: 291-297.
Thiel, E. A., "Managing Epilepsy in Tuberous Sclerosis Complex," J Child Neurol 2004;19:680-686.
"University of Utah doctors: Say 'yes' to cannabis oil for kids," By Kirsten Stewart the Salt Lake Tribune, Nov. 13, 2013, 4 pages.
Zhornitsky & Potvin, "Cannabidiol in Humans—The Quest for Therapeutic Targets," Pharmaceuticals, 5:529-552 (2012).
Vanstraten, A.F. et al., "Update on the Management of Lennox-Gastaut Syndrome," Pediatric Neurology, 47:153-161 (2012).
Young, S., "Marijuana stops child's severe seizures," CNN Health online, Aug. 7, 2013, 4 pages; https://www.cnn.com/2013/08/07/health/charlotte-child-medical-marijuana/index.html#:~:text=The%20first%20time%20Paige%20Figi,seizures%20stopped%20for%20seven%20days.&text=The%20marijuana%20strain%20Charlotte%20and,has%20been%20named%20after%20her.
Tose, L. V. et al., "Isomeric separation of cannabinoids by UPLC combined with ionic mobility mass spectrometry (TWIM-MS)—Part I," International Journal of Spectrometry, 418:112-121 (2017).
Trost, B. M. & Dogra, K., "Synthesis of (−)-$\Delta$9-trans-Tetrahydrocannabinol: Stereocontrol via Mo-Catalyzed Asymmetric Allylic Alkylation Reaction," Organic Letters, 9(5):861-863 (2007).
Van Bakel et al., "The draft genome and transcriptome of *Cannabis sativa*," Genome Biology 2011, 12:R102, 18 pages; http://genomebiology.com/2011/12/10/R102 (Oct. 24, 2011).
Whittle et al., (2001). Prospects for New Cannabis-Based Prescription Medicines. Journal of Cannabis Therapeutics. 1(3-4); doi:10.1300/J175v01, 1(3-4), 23 pages.
Wilkey, R., "'Weed Wars': Five-Year-Old Takes Medical Marijuana on Reality Show (Video)", Dec. 10, 2011, 7 pages; https://www.huffpost.com/entry/weed-wars-five-year-old-smokes-marijuana_n_1140351.
U.S. Appl. No. 62/004,495, filed May 29, 2014, Vangara et al.
U.S. Appl. No. 61/969,070, filed Mar. 21, 2014, Kane et al.
U.S. Appl. No. 14/724,351, filed May 28, 2015, Vangara et al.
Afinitor® (everolimus) tablets, for oral use, and Afinitor Disperz® (everolimus tablets for oral suspension) Prescribing Information, 2009, 49 pages.
ChildNeurologyFoundation.org [online], "Disorder Directory: Learn from the Experts—LGS (Lennon-Gastaut Syndrome)," Child Neurology Foundation, available on or before Sep. 6, 2015, retrieved on May 21, 2018; URL http://www.childneurologyfoundation.org/disorders/lgs-Lennox-gastaut-syndrome, 10 pages.
Capal, J. K. & Franz, D. N., "Profile of everolimus in the treatment of tuberous sclerosis complex: an evidence-based review of its place in therapy," Neuropsychiatric Disease and Treatment, 12:2165-2172 (2016).
Christians, U. et al., "Biomarkers of Immunosuppressant Organ Toxicity after Transplantation—Status, Concepts and Misconceptions," Expert Opin Drug Metab Toxicol., 7(2): 175-200 (2011).
Clinical Trials.Gov [online], Identifier: NCT02544750, "An open-label Extension Trial of Cannabidiol (GWP42003-P, CBD) for Seizures in Tuberous Sclerosis Complex (GWPCARE6)," Sponsor: GW Research Ltd, U.S. National Library of Medicine, Oct. 1, 2018; Retrieved from https://clinicaltrials.gov/ct2/show/NCT02544750, 6 pages.
Clinical Drug Interaction Studies—Cytochrome P450 Enzyme- and Transporter-Mediated Drug Interactions Guidance for Industry, U.S. Department of Health and Human Services, Food and Drug Administration, Center for Drug Evaluation and Research (CDER), Jan. 2020, 27 pages.
Consroe et al,. "Chapter 2: Therapeutic Potential of Cannabinoids in Neurological Disorders," Cannabonioids as Therapeutic Agents, R. Mechoulam, Ed., 1986, pp. 21-49.
Consroe et al., "Open label evaluation of cannabidiol in dystonic movement disorders," International Journal of Neuroscience, 30(4):277-282 (1986); doi: 10.3109/00207458608985678.
Ebrahimi-Fakhari, D. et al., "Cannabidiol Elevates mTOR Inhibitor Levels in Tuberous Sclerosis Complex Patients," (2020) Pediatric Neurology, 12 pages; https://doi.org/10.1016/j.pediatrneurol.2019.11.017.
Epidiolex® (cannabidiol) oral solution, CV, Prescribing Information, 2018, 30 pages; https://www.accessdata.fda.gov/drugsatfda_docs/label/2018/210365lbl.pdf.
Ettienne De Meijer, "The Chemical Phenotypes (Chemotypes) of Cannabis," Chapter 5, Handbook of Cannabis, Handbook of Cannabis, Roger G. Pertwee (ed.), pp. 89-110 (2014).
Expert Statement of Dr. Emma Louise Cheetham in European Application No. EP10743541.5, dated Nov. 4, 2016, 6 pages.
Gillen, D., "How Does Caffeine Affect CBD?", Apr. 21, 2019, available at: https://web.archive.org/web/20191220210719/https://greendoorcbd.com/blogs/news/how-does-caffeine-affect-cbd, 4 pages.
Green Roads CBD Coffee and Tea, Product p. 2023, 5 pages; https://greenroads.com/collections/cbd-tea-cbd-coffee?nfsn=2488702.aa938d.
Grotenhermen et al., "The Therapeutic Potential of Cannabis and Cannabinoids," Dtsch Arztebl Int, 109(29-30): 495-501 (2012); doi:10.3238/arztebl.2012.0495.
Gupta Video 2013, Weed—CNN Special; https://www.youtube.com/watch?v=Z3lMfl1_K6U.
Hauser, N. et al., "High on Cannabis and Calcineurin Inhibitors: A Word of Warning in an Era of Legalized Marijuana," Hindawi Publishing Corporation, Case Reports In Transplantation, vol. 2016, Sep. 6, 2018;2018:7095846. doi: 10.1155/2018/7095846. eCollection 2018, 4 pages.
Iwasaki, I., "Metabolism of Tacrolimus (FK506) and Recent Topics in Clinical Pharmacokinetics," Drug Metab. Pharmacokinet., 22(5):328-335 (2007).
Jaeger, W. et al., "Inhibition of cyclosporine and tetrahydrocannabinol meabolism by cannabidiol in mouse and human microsomes," Xenobiotica, 26(3):275-284 (1996).

(56) References Cited

OTHER PUBLICATIONS

Karler et al., "The anticonvulsant activity of cannabidiol and cannabinol," Life Science, 13:1527-1531 (1973).
Kruk-Slomka et al., "A comparison of mecamylamine and bupropion effects on memory-related responses induced by nicotine and scopolamine in the novel object recognition test in mice," Pharmacological Reports, 66(4):638-646 (2014).
Kurz & Blass, "Use of dronabinol (delta-9-THC) in autism: A prospective single-case-study with an early infantile autistic child," Cannabinoids, 5(4):4-6 (2010).
Laprarie et al., "Cannabidiol is a negative allosteric modulator of the cannabinoid CB1 receptor," British J Pharmacology, 172(20):4790-4805 (2015).
Leino, A. et al., "Evidence of a clinically significant drug-drug interaction between cannabidiol and tacrolimus: A case report," American Journal of Transplantation, 18 (Suppl. 4): 744-745 (2018).
Leo et al., "Antiepileptogenic effects of Ethosuximide and Levetiracetam in WAG/Rij rats are only temporary," Pharmacological Reports, 71:833-838 (2019).
Leo et al., "Cognitive impairment in the WAG/Rij rat absence model is secondary to absence seizures and depressive-like behavior," Progress in Neuropsychopharmacology & Biological Psychiatry, 94:109652 (2019), 16 pages.
Malamut, M., "I Drank CBD Coffee for a Week. Here's What I Did to My Anxiety," Nov. 18, 2019, available at https://www.healthline.com/health/mental-health/i-tried-it-cbd-coffee-anxiety, 16 pages.
Mechoulam et al., "Cannabidiol: an overview of some chemical and pharmacological aspects. Part I: chemical aspects," Chemistry and Physics of Lipids, 121:35-43 (2002).
Montenegro et al., "Efficacy of Clobazam as Add-on Therapy for Refractory Epilepsy: Experience at a US Epilepsy Center," Clinical Neuropharmacology, 31(6):333-338 (2008).
Nair et al., "A simple practice guide for dose conversion between animals and human," Journal of Basic and Clinical Pharmacy, 7:27-31 (2016).
Olyaei, A. J. et al., "Interaction Between Tacrolimus and Nefazodone in a Stable Renal Transplant Recipient," Pharmacotherapy, 18(6):1356-1359 (1998).
Physician's Desk Reference, 63rd Ed., 2009, 423-461, 2192-2194, 2639-2242, 3019-3022.
Romano et al., "Inhibition of colon carcinogenesis by a standardized Cannabis sativa extract with high content of cannabidiol," Phytomedicine, 21:631-639 (2014).
Russo et al., "Pharmacology of Epileptogenesis and Related Comorbidities in the WAG/Rij Rat Model of Genetic Absence Epilepsy," Journal of Neuroscience Methods, 310:54-62 (2018).
Russo et al., "Upholding WAG/Rij Rats as a Model of Absence Epileptogenesis: Hidden Mechanisms and a New Theory on Seizure Development," Neuroscience and Biobehavioral Reviews, 71:388-408 (2016).
Samanta, D., "Cannabidiol: A Review of Clinical Efficacy and Safety in Epilepsy," Pediatric Neurology, 96:24-29 (2019).
Sarkisova et al., "The WAG/Rij Strain: A Genetic Animal Model of Absence Epilepsy with Comorbidity of Depression," Progress in Neuro-Psychopharmacology & Biological Psychiatry, 35 854-876 (2011).
Shih, J. J et al., "Epilepsy treatment in adults and adolescents: Expert opinion, 2016," Epilepsy & Behavior, 69:186-222 (2017).
Subduction Coffee + Hemp, Product p. 2023, 5 pages; https://subductioncoffee.com/?afmc=2j&utm_campaing=2j&utm_source=leaddyno&utm_medium=affiliate.
Sun et al., "Comparative study of organic solvent and water-soluble lipophilic extractives from wheat straw I: yield and chemical composition," J Wood Sci, 49:47-52 (2003).
Thomas et al., "Cannabidiol displays unexpectedly high potency as an antagonist of CB1 and CB2 receptor agonists in vitro," British J Pharmacology, 150(5):613-623 (1988).
Thompson et al., "Comparison of acute oral toxicity of cannabinoids in rats, dogs and monkeys," Toxicology and Applied Pharmacology, vol. 25, Issue 3, pp. 363-372 (1973).
Uliss et al., "The conversion of 3,4-CIS- to 3,4-TRANS-cannabinoids," Tetrahedron, 34:1885-1888 (1978).
Warzak et al., "Caffeine Consumption in Young Children," The Journal of Pediatrics, vol. 158, Issue 3, p. 508-509, Mar. 1, 2011.
Weed Wars, Video I, Dec. 10, 2011, Weed Wars: The Story of Jayden-Andrew DeAngelo; https://www.youtube.com/watch?v=2WizdR5uHj0.
Weed Wars, Video II, May 25, 2013, 3 pages; available at https://www.youtube.com/watch?v=XBX_DB9sw5U.
Nathaniel Morris (of Weed Country on Discovery Channel), Selected Media Examples of Pediatric Applications of Cannabidiol, accessed on Jun. 22, 2023, 6 pages; available at https://www.youtube.com/watch?v=Mw3wiWkbRg8.
Weimer-Kruel, A. et al., "Cannabidiol Interacts Significantly with Everolimus-Report of a Patient with Tuberous Sclerosis Complex," Neuropediatrics, 50(6), 2019, 4 pages; doi:https://doi.org/10.1055/s-0039-1695786.
Yamaori, S. et al., "Potent inhibition of human cytochrome P450 3A isoforms by cannabidiol: Role of phenolic hydroxyl groups in the resorcinol moiety," Life Sciences, 88:730-736 (2011).
Zamberletti et al., "Alterations of prefrontal cortex GABAergic transmission in the complex psychotic-like phenotype induced by adolescent delta-9-tetrahydrocannabinol exposure in rats," Neurobiology of Disease, 63:35-47 (2014).
Notice of Opposition to European Patent Application No. EP15784111.5, Patent No. EP3206716, dated May 10, 2021.
[Anonymous], "GW Pharma—GW Pharmaceuticals Announces New Physician Reports of Epidiolex® Treatment Effect in Children and Young Adults With Treatment-Resistant Epilepsy," Oct. 14, 2014; https://ir.gwpharm.com/news-releases/news-release-details/gw-pharmaceuticals-announces-new-physician-reports-epidiolexr-0, 4 pages.
[Anonymous], "GW Pharmaceuticals Announces Epidiolex Receives Fast Track Designation from FDA for the Treatment of Dravet Syndrome," GW Pharmaceuticals Press Release dated Jun. 6, 2014; http://www.gwpharm.com/GW%20Pharmaceuticals%20Announces%20Epidiolex%20Receives%20Fast%20Track%20Designation%20from%20FDA%20for%20the%20Treatment%20of%20Dravet%20Syndrome.aspx, 5 pages.
[Anonymous], "Salutaris Drops Buy Salutaris Drops—Salutaris Drops," Oct. 12, 2014; http:/web.archive.org/web/20141012130255/http://salutarisdrops.com/buy-salutaris-drops/, 2 pages.
[Anonymous], "GW Pharmaceuticals Receives Orphan Drug Designation by FDA for Epidiolex® in the Treatment of Lennox-Gastaut Syndrome," GW Pharmaceuticals Press Release, Feb. 28, 2014; https://www.gwpharm.com/ir/press-releases/gw-pharmaceuticals-receives-orphan-drug-designation-fda-epidiolexr-treatment, 4 pages.
[Anonymous], "Salutaris Drops Cannabidiol for Aicardi Syndrome—Salutaris Drops," Oct. 12, 2014; http:/web.archive.org/web/20141012220050/http://salutarisdrops.com/cannabidiol-aicardi-syndrome/, 3 pages.
[Anonymous], "GW Pharma Initiates Second Phase 3 Pivotal Study of Epidiolex® (CBD) in Lennox-Gastaut Syndrome," Jun. 11, 2015; https://www.benzinga.com/pressreleases/18/11/g12748407/gw-pharmaceuticals-announces-second-positive-phase-3-pivotal-trial-for, 5 pages.
Booth, "Legalization's opening of medical pot research is dream and nightmare," Denver Post, Dec. 14, 2013, http://www.denverpost.com/ci_24726291/legalizations-opening-medical-pot-research-is-dream-and, 6 pages.
[No Author Listed], "ILAE Proposal for Revised Terminology for Organization of Seizures and Epilepsies," 2010, 2 pages.
[No Author Listed] "Orphan Drug Designation Granted for Epidiolex in Dravet syndrome by the FDA-Seven Expanded Access INDs granted by FDA to US physicians to treat with Epidiolex 125 children suffering from intractable epilepsy syndromes," GW Pharmaceuticals Press Release dated Nov. 14, 2013.
[No Author Listed] "What are the Highest CBD Strains?" accessed Feb. 16, 2017, published Oct. 15, 2014.
[No Author Listed] "Cannabidiol Therapy for Aicardi Syndrome" Aug. 2014, 4 pages.
[No Author Listed] "Convulsive Disorders and Their Interference with Driving," Medicos., Retrieved Feb. 10, 2017, Retrieved from

(56) References Cited

OTHER PUBLICATIONS internet: URL https://www.medicosporlaseguridadvial.com/en/clinical-subjects/neurologic-diseases/convulsive- disorders-and-their-interference-with-driving/, 2014.
[No Author Listed] "Estimating the Maximum Safe Starting Dose in Initial Clinical Trials for Therapeutics in Adult Healthy Volunteers," FDA Guidance for Industry, Jul. 2005.
[No Author Listed] "GW Pharmaceuticals Announces Physician Reports of Epidiolex Treatment Effect in Children and Young Adults with Treatment-resistant epilepsy from Physician-Led Expanded Access Treatment Program," GW Pharmaceuticals Press Release dated Jun. 17, 2014.
[No Author Listed], Cover and Table of Contents, J Pharmacology and Exp Therapeutics, Feb. 2010, 332(2), 4 pages.
[No Author Listed], "Missouri House passes cannabis extract legislation," Kansas City Star, 2014, https://kansascity.com/news/politics-government/article346747.html, 2 pages.
Alger, B. E., "Not too excited? Thank your endocannabinoids," Neuron, 51(4):393-595 (2006).
American Epilepsy Society, Three Studies Shed New Light on the Effectiveness of Cannabis in Epilepsy, Oct. 14, 2014, 2 pages.
Ames, F. R. et al., "Anticonvulsant effect of cannabidiol," S Afr Med J. Jan. 4, 1986; 69(1):14, 1 page.
AAN 67th Annual Meeting Abstract, Apr. 2015; https://www.aan.com/PressRoom/Home/GetDigitalAsset/11570, 1 page.
Annex to the Communication-Opposition for Application No. 10734541.5, dated Jan. 28, 2016.
Arain, A. M., "Pregabalin in the management of partial epilepsy," Neuropsychiatr Dis Treat., 407-13 (2009); Epub Aug. 20, 2009.
Arslan, A. & Tirnaksiz, F., "Self-emulsifying Drug Delivery Systems," F ABAD J Pharm Sci, 38(1):55-64 (2013).
Avoli, M. et al., "Cellular and molecular mechanisms of epilepsy in the human brain," Prog Neurobiol., 77(3):166-200 (2005).
Babayeva et al., "Marijuana Compounds: A Non-Conventional Therapeutic Approach to Epilepsy in Children," J. Addict. Neuropharmacol, 1:1 (2014); doi:10.24966/AAD-7276/100002, 9 pages.
Bakhsh, K., "Pregabalin in the management of partial epilepsy," Miftaah-al-Khazaain, 1930:607-608, with English translation, 4 pages.
Bancaud, et al., "Proposal for Revised Clinical and Electroencephalographic Classification of Epileptic Seizures," Epilepsia, 22(4):489-501 (1981).
Banerjee et al., "Case Report: Aicardi syndrome: A report of five Indian cases," Neurology India, 54(1):91-93 (2006).
Barker-Haliski, M. et al., "How Clinical Development Can, and Should Inform Translational Science," Neuron, 84:582-593 (2014).
Benowitz, N. L. et al., "Metabolic and Psychophysiologic studies of cannabidiol hexobarbital interaction," Clin Pharmacol Ther., 28(1):115-120 (1980).
Benowitz & Jones, "Cardiovascular and metabolic considerations in prolonged cannabinoid administration in man," J Clin Pharm, 21:214S-223S, 1981.
Bertram, E., "The Relevance of Kindling for Human Epilepsy," Epilepsia, 48(Suppl. 2):65-74 (2007).
Bipolar Health Group (Charlotte's Web Hemp Remedy, available online at http:/bipolarhealthgroup.org/index.php/charlottes-web-hemp-remedy/, accessed Sep. 6, 2017.
Bhatt, V. P. & Vashishtha, D. P., "Indigenous plants in traditional healthcare system in Kedarnath valley of western Himalaya," Indian J Tradit Knowl., 7(2):300-310 (2000).
Bhattacharyya, S. et al., "Modulation of mediotemporal and ventrostriatal function in humans by Delta9-tetrahydrocannabinol: a neural basis for the effects of Cannabis sativa on learning and psychosis," Arch Gen Psychiatry, 66(4):442-451 (2009); doi:10.1001/archgenpsychiatry.2009 .17.
Bostanci, M. O. & Bagirici, F., "The effects of octanol on penicillin induced epileptiform activity in rats: an in vivo study," Epilepsy Research, 71:188-194 (2006).
Braida, D. et al., "Post-ischemic treatment with cannabidiol prevents electroencephalographic flattening, hyperlocomotion and neuronal injury in gerbils," Neuroscience Letters., 346:61-64 (2003).
Brown et al., Child Neurology Foundation, "LGS" (Lennox-Gastaut Syndrome), available at http://www.childneurologyfoundation.org/disorders/lgs-lennox-gastaut-syndrome.
Brust, J. C. M. et al., "Marijuana use and the risk of new onset seizures," Trans Am Clin Climatol Assoc., 103:176-181 (1992).
"Cannabidiols: Potential Use in Epilepsy & Other Neurological Disorders." Cannabidiol Conference at NYU School of Medicine, Oct. 2013. NYU Langone Health. Retrieved from the Internet Nov. 2019. <URL: http://faces.med.nyu.edu/research-education/cannabidiol-conference>, 4 pages.
Camfield, "Definition and natural history of Lennox-Gastaut Syndrome," Epilepsia, 52:3-9 (2011).
Campos-Castello, "Rational approach to treatment options for Lennox-Gastaut syndrome," Orphanet, Mar. 2003; https://www.orpha.net/data/patho/GB/uk-Lennox.pdf, 5 pages.
Carlini, et al., "Hypnotic and antiepileptic effects of cannabidiol," J Clin Pharmacol. Aug.-Sep. 1981;21(8-9 Suppl):417S-427S. Medline abstract only.
Castel-Branco, et al., "The Maximal Electroshock Seizure (MES) Model in the Preclinical 98. Assessment of Potential New Anti epileptic Drugs," Methods Find Exp Clin Pharmacol., 31(2): 101-106 (2009).
cdc.gov [online], "2 to 20 years: Girls Stature-for-age and Weight-for-age percentiles," National Center for Health Statistics and National Center for Chronic Disease Prevention and Health Promotion, last modified Nov. 2000, https://www.cdc.gov/growthcharts/data/set1clinical/cj411022.pdf, 1 page.
Charlotte's Web [ online], "Whole-Plant Cannabinoids Outperform Single Molecule Compounds," CWHemp.com, Jan. 11, 2017, retrieved on Jun. 16, 2017, URL https://www.cwhemp.com/blog/whole-plant-cw-hemp-cannabinoids, 6 pages.
Chiron, C. & Dulac, O., "The Pharmacologic Treatment of Dravet Syndrome," Epilepsia, 52 (Suppl. 2):72-75 (2011).
Chiu, P. et al., "The Influence of Cannabidiol and A-Tetrahydrocannabinol on Cobalt Epilepsy in Rats," Epilepsia, 20:365-375 (1979).
Chou, "Theoretical basis, experimental design, and computerized simulation of synergism and antagonism in drug combination studies," Pharmacol Rev, 58(3):621-681 (2006).
Ciccone, "Drop Seizure Frequency in Lennox-Gastaut Decrease With Cannabidiol," Neurology Advisor, Apr. 26, 2017; retrieved from the Internet: URL:https://neurologyadvisor.com/aan-2017-coverage/aan-2017-cannabidiol-reduces-drop-seizures-in-lennox-gasaut-syndrome/article/652931.
Cilio, Maria Roberta, M.D., Ph.D. of the Pediatric Epilepsy and Clinical Neurophysiology for the University of California, San Francisco presents her talk on "CBD in Children with Treatment-Resistant Epilepsies: Planned Trials in Dravet and Lennox-Gastaut Syndromes," at NYU School of Medicine's Cannabidiol Conference (Oct. 4, 2013). Video published online. <http://faces.med.nyu.edu/research-education/cannabidiol-conference>.
Citti et al., "Pharmaceutical and biomedical analysis of cannabinoids: A critical review," Journal of Biopharmaceutical and Biomedical Analysis, 147:565-579 (2018).
Combined Search and Examination Report mailed Jan. 4, 2012 for Application No. GB 1116789.7.
Combined Search and Examination Report mailed Mar. 25, 2011 for Application No. GB 1100043.7.
Combined Search and Examination Report mailed Sep. 5, 2014 for Application No. GB 1414813 .4 .
Combined Search and Examination Report Under Sections 17 and 18 (3) for International Application No. GB1121919.3, dated Feb. 29, 2012.
Combined Search and Examination Report Under Sections 17 and 18 (3) for International Application No. GB 141077 1.8, dated Feb. 27, 2018.
Combined Search and Examination Report Under Sections 17 and 18 (3) for International Application No. GB 1418166.3, dated Jul. 2, 2015.

(56) References Cited

OTHER PUBLICATIONS

Combined Search and Examination Report Under Sections 17 and 18 (3) for International Application No. GB 1418170.5, dated Jul. 2, 2015.
Combined Search and Examination Report Under Sections 17 and 18 (3) for International Application No. GB 1418171.3, dated Jun. 29, 2015.
Combined Search and Examination Report Under Sections 17 and 18 (3) for International Application No. GB 1506550.1, dated Feb. 5, 2016.
Combined Search and Examination Report for GB Application No. GB1611544.6, dated Mar. 29, 2017, 8 pages.
Combined Search and Examination Report for GB Application No. GB1514079.1, dated May 4, 2016, 9 pages.
Combined Search and Examination Report for GB Application No. GB160544.8, dated Jan. 12, 2017, 6 pages.
Combined Search and Examination Report for GB Application No. GB1621480.1, dated Sep. 22, 2017.
Communication of a Notice of Opposition for Application No. 107342541.5 dated Dec. 17, 2014.
Communication Pursuant to Article 94(3) EPC in European Patent Application No. 10734541.5, dated Oct. 23, 2012.
Conry, J. A. et al., "Clobazam in the treatment of Lennox-Gastaut syndrome," Epilepsia, 50:1158-1166 (2009).
Consroe, et al., "Anticonvulsant drug antagonism of delta9tetrahydrocannabinol-induced seizures in rabbits," Res Commun Chem Pathol Pharmacol., 16(1):1-13 (1977).
Consroe, et al., "Anticonvulsant interaction of cannabidiol and ethosuximide in rats," J Pharm Pharmacol., 29(8):500-501 (1977); doi: 10.1111/j.2042-7158.1977.tb11378.x.
Consroe, et al., "Anticonvulsant nature of marihuana smoking," JAMA, 234(3):306-307 (1975).
Consroe, et al., "Cannabidiol—antiepileptic drug comparisons and interactions in experimentally induced seizures in rats," J Pharmacol Exp Ther., 201(1):26-32 (1977).
Consroe, et al., "Controlled clinical trial of cannabidiol in Huntington's Disease," Pharmacology Biochemistry & Behavior, 40:701-708 (1991).
Consroe, et al., "Effects of cannabidiol on behavioral seizures caused by convulsant drugs or current in mice," Eur J Pharmacol., 83(3-4):293-298 (1982).
Consroe, et al. Chapter 12, "Potential Role of Cannabinoids for Therapy of Neurological Disorders." p. 459 in Marijuana Cannabinoids: Neurobiology and Neurophysiology, ed. L. Murphy (1992).
Cortesi, et al., "Potential therapeutical effects of cannabidiol in children with pharmacoresistant epilepsy," Med Hypotheses, 68(4):920-921 2007). Epub Nov. 1, 20066.
Cortez, et al. Chapter 10, "Pharmacologic Models of Generalized Absence Seizures in Rodents," Models of Seizures and Epilepsy, 111-126 (2006).
Crespel, A. et al., "Lennox-Gastaut Syndrome," Chapter 14, in Epileptic Syndromes in Infancy, Childhood, and Adolescence, 5th Edition, ed. M. Bureau, et al., pp. 189-216.
Cunha, et al., "Chronic administration of cannabidiol to healthy volunteers and epileptic patients," Pharmacology, 21(3):175-85 (1980).
Curia et al., "The pilocarpine model of temporal lobe epilepsy," J Neuroscience Methods, 172(2-4):143-157 (2008).
Czapinski, et al., "Randomized 36-month comparative study of valproic acid (VPA), phenytoin (PHT), phenobarbital (PB) and carbamazepine (CBZ) efficacy in patients with newly diagnosed epilepsy with partial complex seizures," J Neurolog Sci., 150:S162 (1997).
Dasa, et al. "Brhat Nighantu Ratnakara (Saligramanighantubhusanam)." vol. IV. 1997:170. Sanskrit. Exhibit 5.
Davis, et al., "A predominant role for inhibition of the adenylate cyclase/protein kinase. A pathway in ERK activation by cannabinoid receptor 1 in NIE-115 neuroblastoma cells," J Biol Chem., 278(49):48973-80 (2003). Epub Sep. 29, 2003.
Davis, et al., "Antiepileptic action of marijuana-active substances," Federation Proceedings, 8:284-5 (1949).
Decision in IPR2017-00503 dated Jul. 7, 2017.
Decision in Opposition proceedings (Art. 101(3)(a) and 106(2) EPC in European Patent Application No. EP2448637, dated Dec. 15, 2016.
Deshpande, et al., "Cannabinoid CB 1 receptor antagonists cause status epilepticus-like activity in the hippocampal neuronal culture model of acquired epilepsy," Neurosci Lett., 41 I(I):1-6 (2007). Epub Nov. 15, 2006.
De Oliveira, et al., "Anticonvulsant activity of β-caryophyllene against pentylenetetrazol-induced seizures," Epilepsy Behav., 56:26-31 (2016); doi: 10.1016/j.yebeh.2015.12.040.
De Meijer, "The Chemical Phenotypes (Chemotypes) of Cannabis," Chapter 5, Handbook of Cannabis, ed. Roger G. Pertwee, pp. 89-110 (2014).
Devinsky, Orrin, M.D. of the Department of Neurology for NYU Langone School of Medicine presents his talk on "Cannabidiols: A Brief History," at NYU School of Medicine's Cannabidiol Conference (Oct. 4, 2013). Video published online. <http://faces.med.nyu.edu/research-education/cannabidiol-conference>.
Devinsky et al., "Epidiolex (Cannabidiol) in Treatment Resistant Epilepsy," Apr. 2015; https://epilepsyontario.org/wp-content/uploads/2015/Epidiolex-Cannabidiol-in-Treatment-Resistant-Epilepsy AAN-POSTER 08Apr2015.pdf, 1 page.
Devinsky, et al., "Cannabidiol: Pharmacology and potential therapeutic role in epilepsy and other neuropsychiatric disorders," Epilepsia, 55(6):791-802 (2014).
Devinsky et al., "Efficacy and safety of Epidiolex (cannabidiol) in children and young adults with treatment-resistant epilepsy: Initial data from expanded access program," Jan. 2015.
Devinsky et al., "Cannabidiol in patients with treatment-resistant epilepsy: an open-label interventional trial," Lancet Neurology, 15(3):270-278 (2015).
Devinsky et al., "Cannabidiol (CBD) significantly reduces drop seizure frequency in Lennox-Gastaut syndrome (LGS): results of a dose-ranging, multi-center, randomized, double-blind, placebo-controlled trial (GWPCARE3)," Epilepsia, 58:S13-S14 (2017).
Devinsky et al., "Trial of Cannabidiol for Drug-Resistant Seizures in the Dravet Syndrome," N Engl J Med, 376(21):2011-2020 (2017).
Di Marzo, Vincenzo, Ph.D. of the Endocannabinoid Research Group Istituto di Chimica Biomolecolare, Consiglio Nazionale delle Ricerche, Pozzuoli, Napoli, Italy presents his talk on "Cannabinoid Pharmacology & Mechanism of Action," at NYU School of Medicine's Cannabidiol Conference (Oct. 4, 2013). Video published online. <http://faces.med.nyu.edu/research-education/cannabidiol-conference>.
Dravet, "The core Dravet syndrome phenotype," Epilepsia, 52 Suppl 2:3-9 (2011); doi: 10.1111/j.1528-1167.2011.02994.x.
Dreifus, et al., "Proposal for Revised Clinical and Electroencephalographic Classification of Epileptic Seizures," Epilepsie., 22:489-501 (1981).
Drugs of the Future, 39(1): 49-56, Jan. 2014 notes Orphan Drug designation for CBD for Lennox-Gastaut Syndrome.
Dulac, "Use of Lamotrigine in Lennox-Gastaut and Related Epilepsy Syndromes," J. Child Neurolog., 12(Supplement 1): S23-S29 (1997).
Dulac, "Vigabatrin in Childhood Epilepsy," J. Child Neurolog., 6(Supplement 2): S30-S37 (1991).
Eadie, "Shortcomings in the current treatment of epilepsy," Expert Rev Neurother., 12(12):1419-27 (2012).
Engel, "Report of the ILAE classification core group," Epilepsia, 47(9):1558-68 (2006).
Engel, "What should be modeled," in Models Seizure Epilepsy, 2006, 14 pages.
Eggers, "Temporal lobe epilepsy is a disease of faulty neuronal resonators rather than oscillators, and all seizures are provoked, usually by stress," Med Hypotheses., 69(6):1284-9 (2007).
Elsohly and Gul, "Constituents of Cannabis Sariva," Chapter 1, Handbook of Cannabis, Roger G. Pertwee, Ed., pp. 3-22 (2014).
EPO Reply to Proprietor's Statement of Grounds of Appeal for European Patent No. EP2448637, dated Sep. 8, 2017, 5 pages.

(56) References Cited

OTHER PUBLICATIONS

EPO Response to the Statement of Grounds of Appeal for European Patent No. EP2448637, dated Sep. 5, 2017, 17 pages.
Ex parte Edelstam, Appeal No. 2016/006358, mail date Jun. 21, 2017 (Year: 2017).
Ex parte Miller, Appeal 2009-011751, mail date Jul. 8, 2010 (Year: 2010).
Examination Report mailed Mar. 18, 2014 for Application No. GB1100043.7.
Expert Statement of Vincenzo Di Marzo for Application No. EP10734541.5 dated Sep. 9, 2016.
Expert Statement of Professor Benjamin J. Whalley for Application No. EP10734541.5 dated Sep. 9, 2016.
Expert Statement of Professor Anthony G. Marson for Application No. EP10734541.5.
FDA, "Warning Letters and Test Results for Cannabidiol-Related Products," 2016 Warning Letters.
FDA, "Warning Letters and Test Results for Cannabidiol-Related Products," 2015 Warning Letters.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
Fariello, "Parenteral Penicillin in Rats: An Experimental Model of Multifocal Epilepsy," Epilepsia, 17:217-222 (1976).
Ferdinand, et al., "Cannabis—psychosis pathway independent of other types of psychopathology," Schizophr Res., 79(2-3):289-295 (2005).
Fisher, et al., "The impact of epilepsy from the patient's perspective I. Descriptions and subjective perceptions," Epilepsy Res.,41(1):39-51 (2000).
French, Jacqueline A., M.D. Professor of Neurology at the NYU Epilepsy Center presents her talk on "Trials for Disease Modifying Therapies in Epilepsy," at NYU School of Medicine's Cannabidiol Conference (Oct. 4, 2013). Video published online. <http://faces.med.nyu.edu/research-education/cannabidiol-conference>.
Friedman, Daniel, M.D. Assistant Professor of Neurology at the NYU Comprehensive Epilepsy Center presents his talk on "Pharmacology of CBD in Humans," at NYU School of Medicine's Cannabidiol Conference (Oct. 4, 2013). Video published online. <http://faces.med.nyu.edu/research-education/cannabidiol-conference>.
Gabor, et al., "Lorazepam versus phenobarbital : Candidates for drug of choice for treatment of status epilepticus," J Epilepsy, 3(1):3-6 (1990).
Gallily, et al., "Overcoming the Bell-Shaped Dose-Response of Cannabidiol by Using Cannabis Extract Enriched in Cannabidiol," Pharmacology & Pharmacy, 6:75-85 (2015).
Gastaut, "Clinical and electroencephalographical classification of epileptic seizures," Epilepsia, 10:Suppl:2-13 (1969).
Gardner [online], "Comes Now Epidiolex (FDA Approves IND Studies of CBD)," BeyondTHC.com, Oct. 22, 2013, retrieved on Jan. 31, 2018, http://www.beyondthc.com/comes-now-epidiolex-fda-approves-ind-studies-of-cbd, 4 pages.
Gedde, Retrospective Case Review of High CBD, Low THC Cannabis Extract (Realm Oil) for Intractable Seizure Disorders, 2013 Realm of Caring Foundation, 4 pages.
Gedde, "Clinical Experience with Cannabis in Treatment-Resistant Pediatric Epilepsy," http://www.theroc.us/images/gedde presentation.pdf, Sep. 9-11, 2014.
Geffrey et al., "Cannabidiol (CBD) Treatment for Refractory Epilepsy in Tuberous Sclerosis Complex," American Epilepsy Society, Annual General Meeting, Abstract, accessed on Jun. 23, 2015; https://www.aesnet.org/meetings_events/annual_meeting_abstracts/view/1868979, 2 pages.
Gedde et al., "Clinical Experience with Cannabis in Treatment-Resistant Pediatric Epilepsy," http://www.theroc.us/images/gedde.presentation.pdf, Sep. 9-11, 2014.
Geffrey et al., "Drug-drug interaction between clobazam and cannabidiol in children with refractory epilepsy," Epilepsia, 56(8):1246-1251 (2015).
Green, "CBD: An Unconventional Therapy," available online at http://nugs.com/article/cbd-anunconventional-therapy.html, published Mar. 24, 2014, 5 pages.
Gresham, et al., "Treating Lennox-Gastaut syndrome in epileptic pediatric patients with third generation rufinamide," Neuropsychiatr Dis Treat., 6:639-645 (2010).
Gross, et al., "Marijuana use and epilepsy: prevalence in patients of a tertiary care epilepsy center," Neurology, 62(11 ):2095-7 (2004).
Guerrini, et al., "Lamotrigine and Seizure Aggravation in Severe Myoclonic Epilepsy," Epilepsia, 39(5):508-512 (1998).
Guimaraes, et al., "Antianxiety effect of cannabidiol in the elevated plus-maze," Psychopharmacology (Berl)., 100(4):558-9 (1990); doi: 10.1007/BF02244012.
Goodman & Gilman, The Pharmacological Basis of Therapeutics (Brunton, Laurence L.; Lazo, John S.; Parker, Keith, eds. (2006); New York: McGraw-Hill. ISBN 0-07-142280-3); Chapter 19, Pharmacotherapy of the Epilepsies.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL https://www.gwpharm.com/about-us/news/gw-pharmaceuticals-announces-epidiolex%C2%AE-receives-fast-track-designation-fda-treatment.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, 8 pages.
GWPharm [online], "GW Pharmaceuticals Provides Update on Orphan Program in Childhood Epilepsy for Epidiolex ®," GW Pharmaceuticals Press Release, Nov. 15, 2013, 5 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, 5 pages.
GWPharm [online], "GW Pharmaceuticals Announces Preliminary Results of Phase 2a Study for its Pipeline Compound GWP42006," GW Pharmaceuticals Press Release, Feb. 21, 2018, 5 pages.
Heinemann, et al., "An Overview of in Vitro Seizure Models in Acute and Organotypic Slices," Chapter 4, 35-44 (2006).
Hess et al., "Cannabidiol as a new treatment for drug-resistant epilepsy in tuberous sclerosis complex," Epilepsia, 57(10):1617-1624 (2016).
Hill, et al., "Δ9-Tetrahydrocannabivarin suppresses in vitro epileptiform and in vivo seizure activity in adult rats." Epilepsia, 51(8):1522-32 (2010); doi: 10.1111/j.1528-1167.2010.02523.x. Epub Feb. 26, 2010.
Hill, "Cannabidivarin-rich cannabis extracts are anticonvulsant in mouse and rat via a CB 1 receptor-independent mechanism," British Journal of Pharmacology, 170(3):679-692 (2013).
Holmes, et al., "Choosing the correct AED: From Animal Studies to the Clinic," Pediatr Neurol. 38(3):151-162 (2008).
Iannotti, et al., "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability," ACS Chem Neurosci., 5(11):1131-41 (2014); doi: 10.1021/cn5000524.
ICE Epilepsy Alliance, The Dravet Syndrome Spectrum, Nov. 2008, 2 pages.
*Insys Development Company, Inc.* v. *GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*Insys Development Company, Inc.* v. *GW Pharma Limited and Otsuka Pharmaceutical Co., Ltd.*, Final Written Decision in IPR2017-00503, U.S. Pat. No. 9,066,920, dated Jan. 3, 2019, 40 pages.

(56) References Cited

OTHER PUBLICATIONS

*Insys Development Company, Inc. v. GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.
*Insys Development Company, Inc. v. GW Pharma Limited and Otsuka Pharmaceutical Co., Ltd.*, Petitioner's Reply to Patent Owner's Response, IPR2017-00503, U.S. Pat. No. 9,066,920, dated Jun. 19, 2018, 6 pages.
*Insys Development Company, Inc. v. GW Pharma Limited and Otsuka Pharmaceutical Co., Ltd.*, Petitioner's Reply to Response in IPR2017-00503, U.S. Pat. No. 9,066,920, dated Jan. 19, 2018.
International Preliminary Report on Patentability in International Application No. PCT/GB2010/051066, dated May 3, 2011.
International Preliminary Report on Patentability for International Application No. PCT/GB2015/053030, dated Apr. 18, 2017.
International Preliminary Report on Patentability for International Application No. PCT/GB2017/052229, dated Feb. 26, 2019, 7 pages.
International Preliminary Report on Patentability for International Application No. PCT/GB2017/052229, dated Oct. 6, 2017, 10 pages.
International Preliminary Report on Patentability for International Application No. PCT/GB2015/051775, dated Aug. 10, 2016.
International Preliminary Report on Patentability for International Application No. PCT/US2017/050868, dated Oct. 11, 2018, 7 pages.
International Search Report and Written Opinion for International Application No. PCT/US2017/050868, dated Aug. 6, 2017, 14 pages.
International Search Report and Written Opinion for International Application No. PCT/US2017/051943, dated Sep. 12, 2017, 10 pages.
International Search Report and Written Opinion for International Application No. PCT/GB2017/051913, dated Sep. 15, 2017, 9 pages.
International Search Report and Written Opinion for International Application No. PCT/GB2017/051914, dated Sep. 12, 2017.
International Search Report and Written Opinion mailed Nov. 16, 2012 for International Application No. PCT/GB2012/052284, dated Mar. 29, 2014.
International Preliminary Report on Patentability mailed Dec. 12, 2013 for International Application No. PCT/GB2012/052284.
International Preliminary Report on Patentability mailed Jun. 9, 2011 for International Application No. PCT/GB2010/051066.
International Preliminary Report on Patentability mailed Sep. 1, 2017 for International Application No. PCT/GB2016/051792.
International Search Report and Written Opinion mailed Aug. 25, 2015 for International Application No. PCT/GB2015/051776.
International Search Report and Written Opinion mailed Aug. 26, 2015 for International Application No. PCT/GB2015/051775.
International Search Report and Written Opinion mailed Dec. 13, 2010 for International Application No. PCT/GB2010/051066.
International Search Report and Written Opinion mailed May 30, 2011 for International Application No. PCT/GB2011/050649.
International Search Report mailed Nov. 16, 2010 for International Application No. PCT/GB2010/051066.
International Search Report mailed Feb. 24, 2012 for International Application No. PCT/GB2012/050002.
IUPHAR/BPS Guide to Pharmacology [online], "Entry for Δ9-tetrahydrocannabidiol," available on or before Mar. 29, 2016, retrieved on Jun. 20, 2018, URL <http://www.guidetopharmacology.org/GRAC/LigandDisplayForward?tab=biology&ligandID=242>, 2 pages.
Iuvone, et al., "Neuroprotective effect of cannabidiol, a non-psychoactive component from Cannabis sativa, on beta-amyloid-induced toxicity in PC12 cells," J Neurochem., 89(1):134-41 (2004).
Izzo, et al., "Non-psychotropic plant cannabinoids: new therapeutic opportunities from an ancient herb," Trends in Pharmacological Sciences, 30(10):515-527 (2009).
Jacobson, "Survey of Current Cannabidiol Use in Pediatric Treatment-Resistant Epilepsy," Apr. 22, 2013; https://www.thcint.com/uploads/1/9/3/7/19371199/cannabidiol_use_in_pediatric_epilepsy.pdf, 1 page.
Jeavons, et al., "Sodium valproate in treatment of epilepsy," Br Med J., 2(5919):584-6 (1974).
Jones et al. [online], Info & Metrics / Article Information,"Cannabidiol Displays Antiepileptic from and Antiseizure Properties in Vitro and in Vivo," J Pharmacol Exp Ther., Feb. 2010, 332(2):569-577, retrieved on Jun. 25, 2018, URL: http://jpet.aspetjournals.org/content/332/2/569/tab-article-info.
Jones et al., "Cannabidiol Displays Antiepileptiform and Antiseizure Properties in Vitro and in Vivo," J Pharmacol Exp Ther., 332(2):559-577 (2010).
Joy, et al., "Marijuana and Medicine. Assessing the Science Base," National Academy Press. Washington D.C., 1999, 170 pages.
Jutras-Aswad, Didier, M.D., M.S. of the Department of Psychiatry for the University of Montreal presents his talk on "CBD in Animal Models and Human Trials of Opiate Abuse," at NYU School of Medicine's Cannabidiol Conference (Oct. 4, 2013). Video published online. <http://faces.med.nyu.edu/research-education/cannabidiol-conference>.
Kahan, et al., "Risk of selection bias in randomized trials," Trials, 16:405 (2015).
Karler, et al., "The cannabinoids as potential antiepileptics," J Clin Pharmacol, 21(8-9 Suppl):437S-447S (1981).
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Katz, Russell ("Rusty"), M.D. former Director of the Division of Neurology Products at the FDA presents his talk on "Dravet and Lennox-Gastaut Syndromes: The Orphan Drug Process," at NYU School of Medicine's Cannabidiol Conference (Oct. 4, 2013). Video published online. <http://faces.med.nyu.edu/research-education/cannabidiol-conference>.
Khan et al., "Key Attributes of TKDL: Laooq-e-Quinnab/Barai Zeequn-Nafs," Khazaain-al-Advia, 1911 (with English translation), 2 pages.
Khan et al., Key Attributes of TKDL: Nushka-e-Qutoor, Muheet-e-Azam, 1887 (with English translation), 2 pages.
Khan et al., "Key Attributes of TKDL: Sufoof-e-Qinnab Barae Waja," Khazaain-al-Adiva, 1911, (with English translation), 5 pages.
Khan et al., "Key Attributes of TKDL: Usaara-e-Qinnab Barai Qoolanj," Khazaain-al-Advia, 1911 (with English translation), 6 pages.
Khan et al., "Key Attributes of TKDL: Zimad-e-Qinnab," Khazaain-al-Adiva, 1911 (with English translation), 5 pages.
Kelley, et al., "Doose syndrome (myoclonic-astatic epilepsy): 40 years of progress," Developmental Medicine & Child Neurology, 52:988-993 (2010).
Klitgaard, et al., "Electrophysiological, neurochemical and regional effects of levetiracetam in the rat pilocarpine model of temporal lobe epilepsy," Seizure, 12(2):92-100 (2003).
Klitgaard, et al., "Evidence for a unique profile of levetiracetam in rodent models of seizures and epilepsy," European Journal of Pharmacology, 353(2):191-206 (1998).
Kramer, et al., "Febrile infection-related epilepsy syndrome (FIRES): pathogenesis, treatment, and outcome: a multicenter study on 77 children," Epilepsia, 52(11):1956-65 (2011); doi:10.1111/j.1528-1167.2011.03250.x. Epub Aug. 29, 2011.
Kuhn et al., "Potent activity of carfilzomib, a novel, irreversible inhibitor of the ubiquitin-proteasome pathway, against preclinical models of multiple myeloma," Blood, 110(9):3281-3290 (2007).
Kwan et al., "Definition of drug resistant epilepsy: consensus proposal by the ad hoc Task Force of the ILAE Commission on Therapeutic Strategies," Epilepsia, 51(6):1069-77 (2010); doi:10.1111/j.1528-1167.2009.02397.x. Epub Nov. 3, 2009. Erratum in: Epilepsia. Sep. 2010;51(9): 1922.

(56) References Cited

OTHER PUBLICATIONS

LeafScience.com [online], "What are the Highest CBD Strains?" Oct. 15, 2014, retrieved on Feb. 16, 2017, URL www.leafscience.com/2014/10/15/highest-cbd-strains/.

Leo, et al., "Cannabidiol and epilepsy: Rationale and therapeutic potential," Pharmacological Research, 107:85-92 (2017).

Letter from Opponent Regarding Oral Proceedings for European Patent No. EP2448637, dated Oct. 20, 2016, 6 pages.

Lewis, "Mystery Mechanisms," The Scientist.com, Jul. 29, 2016, retrieved on Nov. 8, 2017, 2 pages.

Lieu, et al., "Assessment of self-selection bias in a pediatric unilateral hearing loss study," Otolaryngol Head Neck Surg., 142(3):427-433 (2010).

Lindamood and Colasanti, "Effects of delta 9-tetrahydrocannabinol and cannabidiol on sodium-dependent high affinity choline uptake in the rat hippocampus," J Pharmacology Experimental Therapeutics, 213(2):216-221 (1980).

Long, et al., "The pharmacological actions of cannabidiol," Drugs of the Future, 30(7):747-53 (2005).

Loscher and Schmidt, "Modern antiepileptic drug development has failed to deliver: ways out of the current dilemma," Epilepsia, 52(4):657-78 (2011); doi:10.1111/j.1528-1167.2011.03024.x.

Lutz, "On-demand activation of the endocannabinoid system in the control of neuronal excitability and epileptiform seizures," Biochem Pharmacol., 68(9):1691-8 (2004).

Lowenstein, "Chapter 363: Seizures and Epilepsy," Diseases of the Central Nervous System, 2498-2512 (2008).

Luttjohann, et al., "A revised Racine's scale for PTZ-induced seizures in rats," Physiol Behav., 98(5):579-86 (2009); doi:10.1016/j.physbeh.2009.09.005.

Maa et al., "The case for medical marijuana in epilepsy," Epilepsia, 55(6):783-786 (2014).

Mackie, "Cannabinoid receptors as therapeutic targets," Annu Rev Pharmacol Toxicol., 46:101-22 (2006).

Majoosi, et al. Kaamil-al-Sena'ah, Part II, Central Council for Research in Unani Medicine. 2005: 116. Arabic. Exhibit 2.

Malfait, et al. "The nonpsychoactive cannabis constituent cannabidiol is an oral anti-arthritic therapeutic in murine collagen-induced arthritis," PNAS, 97(17):9561-9566 (2000).

Manni et al., "Obstructive Sleep Apnea in a Clinical Series of Adult Epilepsy Patients: Frequency and Features of the Comorbidity," Epilepsia, 44(6):836-840 (2003).

Manno, "Status Epilepticus: Current Treatment Strategies," The Neurohospitalist, 1(1):23-31 (2011).

Mattson, et al., "Comparison of carbamazepine, phenobarbital, phenytoin, and primidone in partial and secondarily generalized tonic-clonic seizures," N. Engl. J. Med, 313(3):145-151 (1985).

Mattson, et al., "Prognosis for total control of complex partial and secondary generalized tonic clonic seizures," Neurology, 47:68-76 (1996).

Mares et al., "Electrical Stimulation-Induced Models of Seizures in Model of Seizures and Epilepsy Asla Pitkanen," Philip A. Schwartzkroin & Solomon L. Moshe, eds., 2004.

Marinol Label retrieved from https://www.accessdata.fda.gov/drugsatfda_docs/label/2006/018651s025s026lbl.pdf.

Martin et al., "Structure-Anticonvulsant Activity Relationships of Cannabidiol Analogs," National Institute on Drug Abuse, Research Monograph Series, 79:48-58 (1987).

McCormick et al., "On the cellular and network bases of epileptic seizures," Annu Rev Physiol., 63:815-46 (2001).

McNamara, "Chapter 19: Pharmacotherapy of the Epilepsies,", Goodman & Gilman's he Pharmacological Basis of Therapeutics 11th ed., McGraw-Hill Companies, pp. 501-525 (2006).

Mechoulam, et al., "Cannabidiol: An Overview of Some Pharmacological Aspects," J Clin Pharmacol, 42:11S-19S (2002).

Mechoulam, et al., Toward drugs derived from cannabis, Naturwissenschaften, 65(4):174-9 (1978).

Merlis, "Proposal for an international classification of the epilepsies," Epilepsia, 1(1):114-9 (1970).

Miller, et al., "Mapping genetic modifiers of survival in a mouse model of Dravet syndrome," Genes, Brain and Behavior, 13:163-172 (2014).

Montouris, "Rational approach to treatment options for Lennox-Gastaut syndrome," Epilepsia, 52:10-20 (2011).

Morard, et al., "Conversion to Sirolimus-Based Immunosuppression in Maintenance Liver Transplantation Patients," Liver Transplantation, 13:658-664 (2007).

Moral, et al., "Pipeline on the Move," Drugs of the Future, 39(1):49-56 (2014).

Morelli et al., "The effects of cannabidiol and its synergism with bortezomib in multiple myeloma cell lines. A role for transient receptor potential Vanilloid type-2," Blood, 110(9):3281-3290 (2014).

MyVirtualMedicalCentre [online], "Aicardi syndrome," mymc.com, Feb. 2004, retrieved on Jan. 25, 2019 at https://www.myvmc.com/diseases/aicardi-syndrome/, 6 pages.

Nabissi et al., "Cannabinoids synergize with carfilzomib, reducing multiple myeloma cells viability and migration," Oncotarget, 7:77553 (2016).

Ng et al., "Illicit drug use and the risk of new-onset seizures." Am J Epidemiol., 132(1):47-57 (1990).

Neto, et al., "The role of polar phytocomplexes on anticonvulsant effects of leaf extracts of Lippia Alba (Mill.) N.E. Brown chemotypes," J. Pharm Pharmacol. 61(7):933-9 (2009).

Notice of Allowance in U.S. Appl. No. 13/380,305, mailed Dec. 10, 2014.

Notice of Allowance in U.S. Appl. No. 13/380,305, mailed Mar. 19, 2015.

Notice of Appeal in European Patent No. EP2448637, dated Feb. 14, 2017.

Notice of Opposition to a European Patent No. EP2448637, Dated Dec. 5, 2014.

Oakley, et al., "Dravet Syndrome Insights into pathophysiology and therapy from a mouse model of Dravet syndrome," Epilepsia 52(Suppl. 2):59-61 (2011).

Obay et al., "Antiepileptic effects of ghrelin on pentylenetetrazol-induced seizures in rats," Peptides, 28(6): 1214-9 (2007). Epub Apr. 1, 20079.

Office Action in U.S. Appl. No. 13/380,305, dated Aug. 25, 2014.

Opponent Response to the Preliminary Opinion of the Opposition Division in European Patent No. EP2448637, dated Jun. 23, 2016.

Opponent Response dated to September the 9, Preliminary 2016, 25 Opinion pages of the Opposition Division in European Patent No. EP2448637, dated Sep. 9, 2016.

Opponent Response to the Written Submissions in European Patent No. EP2448637, dated Oct. 12, 2016.

Opponent Response to the Written Submissions in European Patent No. EP2448637, dated Oct. 20, 2016.

Opponent Response to the Written Submissions in European Patent No. EP2448637, dated Nov. 4, 2016.

Patent Owners' Preliminary Response for IPR2017-00503 dated Apr. 11, 2017.

Pelliccia, et al., "Treatment with CBD in oily solution of drug-resistant paediatric epilepsies," Available online Sep. 2, 2010, Retrieved Jun. 30, 2015; http://www.gwpharm.com/uploads/pelliccia-2002-treatmentwithcbdinoilysolutionofdrug-resistantpediatricepilepsies.pdf.

Pereira, et al., "Study pharmacologic of the GABAergic and glutamatergic drugs on seizures and status epilepticus induced by pilocarpine in adult Wistar rats," Neurosci Lett., 419(3):253-7 (2007). Epub Apr. 13, 2007.

Perucca, "Cannabinoids in the Treatment of Epilepsy: Hard Evidence at Last?" Journal of Epilepsy Research, 7(2):61-76 (2017).

Pertwee, "Cannabinoid receptor ligands: clinical and neuropharmacological considerations, relevant to future drug discovery and development," Expert Opin Investig Drugs, 9(7):1553-71 (2000).

Pertwee, "The diverse CB1 and CB2 receptors pharmacology of three plant cannabinoids: Alpha9 Tetrahydrocannabinol, cannabidiol and alpha9-tetrahydrocannabivarin," Br. J. Pharmacol., 153(2):199-215 (2008).

(56) References Cited

OTHER PUBLICATIONS

Pertwee, "The Pharmacology and Therapeutic Potential of Cannabidiol," Cannabinoids, Chapter 3, DiMarzo, V. (Ed.), pp. 32-83 (2004).
Petition for Inter Partes Review U.S. Pat. No. 9,066,920 dates Dec. 16, 2016.
Petrocellis, et al., "Effects of cannabinoids and cannabinoid-enriched Cannabis extracts on TRP channels and endocannabinoid metabolic enzymes," British Journal of Pharmacology, 163: 1479-1494 (2011).
Pohl, et al., "Effects of flunarizine on Metrazol-induced seizures in developing rats," Epilepsy Res., 1(5):302-5 (1987).
Porter et al., "Report of a parent survey of cannabidiol-enriched cannabis use in pediatric treatment-resistant epilepsy," Epilepsy Behav., 29(3):574-577 (2013).
Porter et al., "Randomized, multicenter, dose-ranging trial of retigabine for partial-onset seizures," Neurology, 68(15):1197-1204 (2007).
Potter, "Cannabis Horticulture," Chapter 4, Handbook of Cannabis, ed. Roger G. Pertwee, pp. 65-88 (2014).
Poortman-Van Der Meer, "A contribution to the improvement of accuracy in the quantitation of THC," Forensic Science International, Apr. 1999, 101(1):1-8.
Pouton, "Lipid formulations for oral administration of drugs: non-emulsifying, self-emulsifying and 'self-micro emulsifying' drug delivery systems," Eur J Pharm Sci, 11(Suppl. 2):S93-S98 (2000).
Press, et al., "Parental reporting of response to oral cannabis extracts for treatment of refractory epilepsy," Epilepsy Behav. Apr. 2015;45:49-52. doi: 10.1016/j.yebeh.2015.02.043. Epub Apr. 3, 2015.
Pruitt et al., "Ethanol in Liquid Preparations Intended for Children," Pediatrics, 73(3):405-407 (1984).
Raab et al., "Multiple myeloma," Lancet, 374(9686):324-339 (2009).
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani, et al. "Epilepsy in Aicardi—Goutieres syndrome," Official J Eur Paediatric Neurology Society, 18:30-37 (2014).
Rauca, et al. "The role of superoxide dismutase and alpha-tocopherol in the development of seizures and kindling induced by pentylenetetrazol—influence of the radical scavenger alpha-phenyl-N-tert-butyl nitrone," Brain Res. May 29, 2004;1009(1-2):203-12.
Resstel et al., "5-HT1A receptors are involved in the cannabidiol-induced attenuation of behavioural and cardiovascular responses to acute restraint stress in rats," Br J Pharmacol. Jan. 2009;156(1):181-8.
Reply of the Patent Proprietor to the Notice(s) of Opposition in European Patent No. 2448637, dated May 28, 2015, 12 pages.
Reply to Communication from the examining Division in European Patent Application No. 10734541.5 dated Feb. 15, 2013, 54 pages.
Reply to EPO Communication in European Patent No. EP2448637, dated Nov. 2, 2016, 45 pages.
Reply to Opponent's Written Submission in European Patent No. EP2448637, dated Nov. 4, 2016, 13 pages.
Reply to Opponent's Written Submission in European Patent No. EP2448637, dated Oct. 18, 2016, 5 pages.
Reply to Preliminary Opinion and Opponent's Observations in European Patent No. EP2448637, dated Sep. 9, 2016, 65 pages.
Request for Continued Examination with the Amendment and Information Disclosure Statement in Application No. 13,380,305, filed Mar. 2, 2015, 3 pages.
Rohrback, Brian G., Ph.D, MBA President of Infometrix, Inc. presents his talk on "Assays of Cannabinoids," at NYU School of Medicine's Cannabidiol Conference (Oct. 4, 2013). Video published online. <http://faces.med.nyu.edu/research-education/cannabidiol-conference>.
Rosenberg et al., "Cannabinoids and Epilepsy," Neurotherapeutics, 12(4):747-768 (2015).
Rosenkrantz et al., "Oral and Parenteral Formulations of Marijuana Constituents," J Pharm Sci, 61(7):1106-1112 (1972).
Russo, "Taming THC: potential cannabis synergy and phytocannabinoid-termoid entourage effects," British J. of Pharm. 1333 (2011).
Rubio, et al. "In vivo Experimental Models of Epilepsy," Central Nervous System Agents in Medicinal Chemistry, 10:298-309, 2010.
Sadanandasarma et al., Rasatarangini. 11th Ed. 1979:720-3. Sanskrit.
Sander, "The epidemiology of epilepsy revisited." Curr Opin Neural. Apr. 2003; 16(2): 165-70.
Sastri et al., Anandakandam. 1st Edition. 1952:241. Sanskrit.
Screenshot confirming date of Epidiolex (Cannabidiol) in Treatment Resistant Epilepsy, Apr. 2015; https://epilepsyontario.org/wp-content/uploads/2015/Epidiolex-Cannabidiol-in-Treatment-Resistant-Epilepsy AAN-POSTER 08Apr2015.pdf, 1 page.
Scuderi et al., "Cannabidiol in medicine: a review of its therapeutic potential in CNS disorders," Phytother Res., 23(5):597-602 (2009).
Shukla. [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva et al., "Position Statement on the Use of Medical Cannabis for the Treatment of Epilepsy in Canada," Can J. Neurol. Sci., 33:783-786 (2006).
Smith, R. M., "Identification of Butyl Cannabinoids in Marijuana," Journal of Forensic Sciences, 42:610-618 (1997).
Sperling et al., "Carisbamate as adjunctive treatment of partial onset seizures in adults in two randomized, placebo-controlled trials," Epilepsia, 51(3):333-343 (2010).
Stafstrom et al., "Models of Pediatric Epilepsies: Strategies and Opportunities," Epilepsia, 47(8):1407-1414 (2006).
Statement of Grounds of Appeal for European Application No. 10734541.5 in the name of GW Pharma and Otsuka Pharmaceutical Co. Limited Appellant/Opponent: Insys Therapeutics Inc., dated Apr. 21, 2017.
Statement of Grounds of Appeal for European Application No. 10734541.5 on behalf of the Proprietors: GW Pharma Limited and Otsuka Pharmaceutical CO Limited, dated Apr. 12, 2017.
Stephenson, "In Memoriam: Professor Jean Aicardi (1926-2015)," Pediatric Neurology, Jan. 2016, 54:3-4.
Stott et al., "Cannabinoids for the pharmaceutical industry," Euphytica, 140:83-93 (2004).
Strickley, "Solubilizing Excipients in Oral and Injectable Formulations," Table VIII, Pharmaceutical Research, 21(2):201-230 (2004).
Study NCT02224690—A Study to Investigate the Efficacy and Safety of Cannabidiol (GWP42003-P; CBD) AS Adjunctive Treatment for Seizures Associated With Lennox-Gastaut Syndrome in Children and Adults, Aug. 22, 2014; https://clinicaltrials.gov/ct2/show/NCT02224690, 1 page.
Supplemental Expert Statement of Professor Benjamin J. Whalley, dated Nov. 4, 2016, 9 pages.
Swann et al., The effects of seizures on the connectivity and circuitry of the developing brain. Ment Retard Dev Disabil Res Rev. 2004; 10(2):96-100.
Tanya Lewis, Mystery Mechanisms, The Scientist Magazine, Jul. 29, 2016.
Third Party Observations for Application No. AU20 I 2314128, mailed Mar. 19, 2015.
Third Party Observations for Application No. EP10734541.5, mailed Apr. 3, 2017.
Third Party Observations for Application No. EP1712658.1, mailed Nov. 22, 2013.
Third Preliminary Amendment under 37 C.F.R. 1.115 for U.S. Appl. No. 13/380,305, dated May 23, 2014, 4 pages.
Thomas et al., "Evidence that the plant cannabinoid Delta9-tetrahydrocannabivarin is a cannabinoid CBI and CB2 receptor antagonist," Br J Pharmacol., 146(7):917-926 (2005).
Thurman et al., "Standards for epidemiologic studies and surveillance of epilepsy," Epilepsia, 52 (Suppl 7):2-26 (2011).
Thumma et al., "Influence of plasticizers on the stability and release of a prodrug of ./19-tetrahydrocannabinol incorporated in poly (ethylene oxide) matrices," Eur J Pharmaceutics and Biopharmaceutics, 70(2):605-614 (2008).
Thurstone, "Avoid Charlotte's Web for Epilepsy," Jun. 26, 2014, URL <http://drthurstone.com/charlotted-web-not-safest-option-epilepsy-treatment/>, 4 pages.

(56) References Cited

OTHER PUBLICATIONS

Transcript of Dr. H. Steven White's deposition, dated Dec. 29, 2017.
Trembly & Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.
Turkanis et al., "An Electrophysiological Analysis of the Anticonvulsant Action of Cannabidiol on Limbic Seizures in Conscious Rats," Epilepsia., 20:351-363 (1979).
Usami et al., "Synthesis and pharmacological evaluation in mice of halogenated cannabidiol derivatives," Chem Pharm Bull (Tokyo), 47(11):1641-1645 (1999).
Unimed Pharmaceuticals, Inc., "Marinol®," Jul. 2006 <https://www.accessdata.fda.gov/dmgsatfdadocs/label/2006/018651 s025s026lbl.pdf>, 11 pages.
USPTO Decision on Appeal in U.S. Appl. No. 10/318,659 (Appeal 2009-011751), dated Jul. 8, 2010, 23 pages.
USPTO Decision on Appeal in U.S. Appl. No. 13/698,730 (Appeal 2016-006358), dated Jun. 21, 2017, 6 pages.
USPTO Information Disclosure Statement Form PTO-1449 for U.S. Appl. No. 13/380,305, dated Nov. 24, 2014, 8 pages.
Utah.gov [online], "2nd Agenda Controlled Substances Advisory Committee Meeting," Nov. 12, 2013, URL <https://www.utah.gov/pmn/files/81459.pdt>, 63 pages.
Van Rijckevorsel, "Treatment of Lennox-Gastaut syndrome: overview and recent findings," Neuropsychiatr Dis Treat. Dec. 2008; 4(6): 1001-1019.
Van Straten et al., "Update on the Management of Lennox-Gastaut Syndrome," Pediatric Neurology, 47:153-161 (2012).
Velasco et al., "Anticancer mechanisms of cannabinoids," Curr Oncol, 23(2):S23-S32 (2016).
Velisek, "Models of Chemically-Induced Acute Seizures," Models Seizure Epilepsy, 127-152 (2006).
Veliskova, Chapter 48 "Behavioral Characterization of Seizures in Rates," Model Seizures Epilepsy, 601-611 (2006).
Vollner et al., Haschisch XX: Cannabidivarin, ein neuer Haschisch-Inhaltsstoff. Tetrahedron Lett. 1969;10(3):145-7.
Wahle et al., "Development of tolerance to the anticonvulsant effect of valproate but not to ethosuximide in a rat model of absence epilepsy," Eur J Pharma. May 1990; 181(1-2):1-8.
Wallace et al., "Pharmacotherapy for Dravet Syndrome," Pediatr. Drugs, 18:197-208 (2016).
Velisek, L., "Models of Chemically-Induced Acute Seizures," In Models of Seizures and Epilepsy, 127-152, 2006.
Wallace et al., "Assessment of the role of CB 1 receptors in cannabinoid anticonvulsant effects," Eur J Pharmacol. Sep. 2, 20018;428(1):51-7.
Weston et al., "Tetrahydrocannabivarin exhibits anticonvulsant effects in a piriform cortical brain slice model of epileptiform activity." Pro British Pharm Soc 75th Anniv Meeting. Dec. 31, 2006 Found on: http://www.pA2online.org/abstract/abstract.jsp?abid=28533. Abstract Only. 1 Page.
Whalley, Benjamin J. Ph.D. of the University of Reading presents his talk on "Cannabis and Epilepsy: Cannabidiol (CBD) and Cannabidavarin (CBDV) in Preclinical Models of Seizure and Epilepsy," at NYU School of Medicine's Cannabidiol Conference (Oct. 4, 2013). Video published online. <http://faces.med.nyu.edu/research-education/cannabidiol-conference>.
"When to Expect Results from CW Hemp Oil", downloaded Sep. 5, 2017, https://www.cwhemp.com/blog/expecting-results-from-hemp.
Wikipedia.org [online], "Cannabinoid," Wikipedia, Apr. 2003, retrieved on Mar. 1, 2017, URL <https://en.wikipedia.org/wiki/Cannabinoid>, 15 pages.
Williams, "The Key to Healing Broken Bones May be Found in This Illegal Drug," Jul. 25, 2015; https://www.fool.com/investing/high-growth/2015/07/25/the-key-to-healing-broken-bones-may-be-found-in-th.aspx#:~:text=As%20published%20in%20the%20Journal,rats%20in%20just%20eight%20 weeks, 5 pages.

Wingerchuk, "Cannabis for medical purposes: cultivating science, weeding out the fiction," Lancet. Jul. 24-30, 2004;364(9431):315-6.
Wright et al., Cannabidiol (CBD) in Dravet Syndrome: A Randomised, Dose-Ranging Pharmacokinetics and Safety Trial (GWPCARE1), Epilepsia, 58(Suppl. 5):S5-S199 (2017), p0240 Abstract, 1 page.
Written Opinion for International Application No. PCT/GB2010/0051066, dated Nov. 22, 2010, 4 pages.
Yu et al., "Reduced sodium current in GABAergic interneurons in a mouse model of severe myoclonic epilepsy in infancy," Nature Neuroscience, 9(9):1142-1149 (2006).
Yuriev, "Endogenic cannabinoid system is a new perspective object of pharmacotherapeutic effect to disease of nervous system," Ukrainsky Metodichny Chasopis, 6(50):21-29 (2005) (with English Abstract).
Zhao et al., "Chapter 27: Repetitive Seizures in the Immature Brain," Models of Seizures and E[epilepsy, 341-350 (2006).
Zuardi et al., "Cannabidiol, a Cannabis sativa constituent, as an antipsychotic drug," Braz J Med Biol Res., 39(4):421-429 (2006).
Zuardi et al., "Cannabidiol: from an inactive cannabinoid to a drug with wide spectrum of action," Rev Bras Psiquiatr, 30(3):271-280 (2008).
U.S. Appl. No. 62/154,660, filed Apr. 29, 2015, Vangara et al.
Aker, R. G. et al., "Chemically Induced Experimental Models of Absence Epilepsy," Chemical-Induced Seizures: Mechanisms, Consequences and Treatment, Chapter 6, 2011, pp. 67-79.
Allen, J. W., "Clobazam as an adjunctive treatment in refractory epilepsy," British Medical Journal, 286:1246-1247 (1983).
Arik, A. E. et al., "Effect of levetiracetam on penicillin induced epileptic activity in rats," Acta Neurobiol Exp, 74:266-275 (2014).
[No Author Listed], "Photo Release—Kannaway Back office Goes Live CBD-Rich Hemp Oil Products Offered for Sale," May 7, 2014, Globe Newswire, https://www.globenewswire.com/en/news-release/2014/05/07/634020/30927/en/Photo-Release-Kannaway-Back-Office-Goes-Live-CBD-Rich-Hemp-Oil-Products-Offered-for-Sale.html, 6 pages.
[No Author Listed], GW and Otsuka Enter into Gobal Cannabinoid Research Collaboration, News Release, Jul. 9, 2007; https://www.otsuka.co.jp/en/company/newsreleases/2007/20070709_1.html, 4 pages.
[No Author Listed], License Agreement between GW Pharma and GW Pharmaceuticals, PLC and Otsuka, Feb. 2007; https://www.sec.gov/Archives/edgar/data/1351288/000104746913003351/a2213875zex-10_16.htm, 63 pages.
Andre, E. S. et al., "Spontaneous absence-like activity in Wistar rats: Behavioral and electrographic characteristics and the effects of antiepileptic drugs," Acta Scientiarum. Biological Sciences, 36(2):231-239 (2014).
Astruc-Diaz, F., "Cannabinoids delivery systems based on supramolecular inclusion complexes and polymeric nanocapsules for treatment of neuropathic pain," Université Claude Bernard—Lyon I, 2012, submitted on Jan. 23, 2014; https://tel.archives-ouvertes.fr/tel-00935588 [accessed Nov. 1, 2019], 278 pages.
Bacca, A., "HempVap from HempMedsPX," Mar. 10, 2014; https://cannabisnow.com/hempvap-from-hempmedspx/, 3 pages.
Barton, M. E. et al., "Pharmacological characterization of the 6 Hz psychomotor seizure model of partial epilepsy," Epilepsy Research, 47:217-227 (2001).
Bhattacharyya, S. et al., "Opposite Effects of delta-9-Tetrahydrocannabinol and Cannabidiol on Human Brain Function and Psychopathology," Neuropsychopharmacology, 35:764-774 (2010).
Bialer, M. & White, S., "Key factors in the discovery and development of new antiepileptic drugs," Nat Rev Drug Discov, 9(1):68-82 (2010); doi: 10.1038/nrd2997.
Bowman et al., "Epilepsy," Encyclopedia of Life Sciences, 1, 2001; www.els.net, 8 pages.
Bromfield, E. B., Cavazos, J. I., Sirven (Ed.,), An Introduction to Epilepsy [Internet], West Hartford, CT, American Epilepsy Society; 2006, PMID: 20821849, 187 pages.
Carlini, E. A. et al., "Anticonvulsant Activity of Four Oxygenated Cannabidiol Derivatives," Research Communications in Chemical Pathology and Pharmacology, 12(1), Sep. 1975, 15 pages.
Charlotte's Web [online], "When to expect Results from CW Hemp Oil, " Mar. 13, 2017, retrieved on May 21, 2018, URL https://www.cwhemp.com/blog/expecting-results-from-hemp, 6 pages.

(56) References Cited

OTHER PUBLICATIONS

Cholongitas et al., "Systematic review: The model for end-stage liver disease—should it replace Child-Pugh's classification for assessing prognosis in cirrhosis?" Aliment Pharmacol Ther, 22(11-12):1079-89 (2005); doi: 10.1111/j.1365-2036.2005.02691.x.
ClinicalTrials.gov archive, History of Changes for Study: NCT02324673, National Institute of Health U.S. National Library of Medicine (Dec. 19, 2014), https://classic.clinicaltrials.gov/ct2/history/NCT02324673?V_1=View#StudyPageTop, 13 pages.
Consroe et al., "Antiepileptic Potential of Cannabidiol Analogs," J Clin Pharmacol., 21:428S-436S (1981).
Consroe et al., "Assay of Plasma Cannabidiol by Capillary Gas Chromatography/Ion Trap Mass Spectroscopy Following High-Dose Repeated Daily Oral Administration in Humans," Pharmacology Biochemistry & Behavior, 40:517-522 (1991).
Costa, B. et al., "Oral anti-inflammatory activity of cannabidiol, a non-psychoactive constituent of cannabis, in acute carrageenan-induced inflammation in the rat paw," Naunyn-Schmiedeberg's Arch Pharmacol, 369:294-299 (2004).
Crowther et al., "The Medication of Cannabis," The transcript of a Witness Seminar held by the Wellcome Trust Centre for the History of Medicine at UCL, London, on Mar. 24, 2009; http://qmro.qmul.ac.uk/xmlui/handle/123456789/2822, 90 pages.
De Deyn et al., "Chemical models of epilepsy with some reference to their applicability in the development of anticonvulsants," Epilepsy Research, 12:87-110 (1992).
Derosa et al., "Chapter XI: Epilepsy," Significant Pharmaceuticals Reported in US Patents, 1st Edition, May 2007, 10 pages.
Dos Santos, R. G. et al., "Phytocannabinoids and epilepsy," Journal of Clinical Pharmacy and Therapeutics, 40:135-143 (2015).
Evans, Randolph W., Neurology Case Studies, Neurol Clin 24, xi-xii, 2006, 2 pages.
FDA Guidance for Industry: Botanical Drug Development, U.S. Dept. of Health, and Human Services: Food and Drug Administration, Dec. 2016, 34 pages.
FDA Guidance for Industry: Q11 Development and Manufacture of Drug Substances, U.S. Dept. of Health and Human Services: Food and Drug Administration, Nov. 2012, 36 pages.
FDA Good Review Practice: Clinical Review of Investigational New Drug Applications, Office of New Drugs in the Center for Drug Evaluation and Research at the Food and Drug Administration, Dec. 2013, 113 pages.
Fryar, C. D. et al., Anthropometric reference data for children and adults: United States, 2011-2014, National Center for Health Statistics. Vital Health Statistics, 3(39), 2016, 46 pages.
Galetin et al., "Multisite Kinetic Analysis of Interactions Between Prototypical CYP3A4 Subgroup Substrates: Midazolam, Testosterone, and Nifedipine," Drug Metabolism and Disposition, 31(9):1108-1116 (2003).
Gaston, T. E. et al., "Quality of life in adults enrolled in an open-label study of cannabidiol (CBD) for treatment-resistant epilepsy," Epilepsy & Behavior, 95:10-17 (2019).
Gedde & Maa, "Whole Cannabis Extract of High Concentration Cannabidiol May Calm Seizures in Highly Refractory Pediatric Epilepsies," American Epilepsy Society, 67th Annual Meeting, Dec. 6-10, 2013. Abstract.
Goldenberg, M. M., "Overview of Drugs Used For Epilepsy and Seizures," P & T, 35(7):392-415 (2010).
Greaves et al., "First Dose of Potential New Medicines to Humans: How Animals Help," Nature Reviews Drug Discovery, 3:226-236 (2004).
Gupta, S., "Why I changed my mind on weed," Aug. 8, 2013; https://www.cnn.com/2013/08/08/health/gupta-changed-mind-marijuana/index.html, 8 pages.
Ha et al., "Epilepsy: Treatment and Management," US Pharm., 38(1):35-39 (2013).
Hancock, E. C. & Cross, J. H., "Treatment of Lennox-Gastaut syndrome (Review)," Cochrane Database of Systematic Reviews, 2013, Issue 2. Art. No. CD003277, doi: 10.1002/14651858.CD003277.pub3., 35 pages.
Hazenkamp, A. et al., "Quantitative Analysis of Cannabinoids from *Cannabis sativa* Using H-NMR," Chem. Pharm. Bull., 52(6):718-721 (2004).
Hazenkamp, A., "Cannabis; extracting the medicine," Doctoral Thesis, 1976, Proefschrift Universiteit Leiden; https://extractionmagazine.com/wp-content/uploads/2018/06/Cannabis-extracting-the-medicine-Arno-Hazekamp-Thesis.pdf, 187 pages.
Herlopian, A. et al., "Cannabidiol in treatment of refractory epileptic spasms: An open label study," Epilepsy & Behavior, 106:106988 (2020), 7 pages; https://doi.org/10.1016/j.yebeh.2020.106988.
Hussain et al., "Perceived efficacy of cannabidiol-enriched cannabis extracts for treatment of pediatric epilepsy: A potential role for infantile spasms and Lennox—Gastaut syndrome," Epilepsy & Behavior, 47:138-141 (2015).
Ilegal Trailer, YouTube video, Mar. 27, 2014; https://www.youtube.com/watch?v=CtJJ1pzMKxs, 5 pages.
Insys Therapeutics Submits Drug Master File for Cannabidiol Active Pharmaceutical Ingredient (API), Marketwired, May 29, 2014; https://www.biospace.com/article/releases/insys-therapeutics-submits-drug-master-file-for-cannabidiol-active-pharmaceutical-ingredient-api-/, 5 pages.
Insys Therapeutics Commences Dosing in Phase 1/2 Safety and Pharmacokinetic Study of Cannabidiol Oral Solution in Pediatric Epilepsy Patients, BioSpace (Apr. 23, 2015); https://www.biospace.com/article/releases/insys-therapeutics-commences-dosing-in-phase-1-2-safety-and-pharmacokinetic-study-of-cannabidiol-oral-solution-in-pediatric epilepsy-patients-/, 3 pages.
Insys Therapeutics, Inc., Quarterly Report Form Q-10, U.S. Securities and Exchange Commission, Mar. 31, 2014; insy20140331_10q.htm, 42 pages.
Insys Therapeutics, Inc., Corporate Integrity Agreement and Conditional Exclusion Release, 2014, 100 pages.
Koek et al., "Treatment-refractory posttraumatic stress disorder (TRPTSD): a review and framework for the future," Progress in Neuro-Psychopharmacology & Biological Psychiatry, 70:170-218 (2016).
Leite et al., "New insights from the use of pilocarpine and kainate models," Epilepsy Research, 50:93-103 (2002).
Lodzki et al., "Cannabidiol-transdermal delivery and anti-inflammatory effect in a murine model," Journal of Controlled Release, 93:377-387 (2003).
Mead et al., "The Untold Story of the Cannabidiol (CBD) Revolution," US Neurology, 2018; 14(Suppl. 3):2-8. Published Online: Oct. 16, 2018.
Mechoulam et al., "Hashish-I: The Structure of Cannabidiol," Tetrahedron, 19:2073-2078 (1963).
Mudigoudar et al., "Emerging Antiepileptic Drugs for Severe Pediatric Epilepsies," Semin Pediatr Neurol, 23:167-179 (2016).
Pertwee, "Cannabidiol as a potential medicine," In: Mechoulam, R. (eds) Cannabinoids as Therapeutics. Milestones in Drug Therapy MDT (2005), pp. 47-65, Birkhäuser Basel. https://doi.org/10.1007/3-7643-7358-X_3.
Rison, R. A., "How to write a neurology case report," Journal of Medical Case Reports, 10:91 (2016); doi:10.1186/s13256-016-0867-x, 5 pages.
Rosenkrantz et al., "Inhalation, Parenteral and Oral LD50 Values of $\Delta^9$-Tetrahydrocannabinol in Fischer Rats," Toxicology and Applied Pharmacology, 28:18-27 (1974).
Samara et al., "Pharmacokinetics of Cannabidiol in Dogs," Drug Metabolism and Disposition, 16(3):469-472 (1988).
Sands, T. T. et al., "Long-Term Safety, Tolerability, and Efficacy of Cannabidiol in Children with Refractory Epilepsy: Results from an Expanded Access Program in the US," CNS Drugs, 33:47-60 (2019); https://doi.org/10.1007/s40263-018-0589-2.
Sasidharan, S. et al., "Extraction, Isolation and Characterization of Bioactive Compounds from Plants' Extracts," Afr J Tradit Complement Altern Med., 8(1):1-10 (2018).
Schafroth et al., "$\Delta$9-cis-Tetrahydrocannabinol: Natural Occurrence, Chirality, and Pharmacology," Journal of Natural Products, 84:2502-2510 (2021).

(56) References Cited

OTHER PUBLICATIONS

Schwieterman, M. L. et al., "Strawberry Flavor: Diverse Chemical Compositions, a Seasonal Influence, and Effects on Sensory Perception," PLoS One, 9(2): e88446 (2014); doi:10.1371/journal.pone. 0088446, 12 pages.

Sirven et al., Finding the Best Dosage of Medication, Epilepsy Foundation (Mar. 19, 2014); https://www.epilepsy.com/treatment/medicines/finding-best-dosage, 11 pages.

Sluss, R. J., "Comparison of Artificial Flavors in Commercial Products and Actual Natural Flavor via Gas Chromatography Mass Spectroscopy Data." (2009). Electronic Theses and Dissertations. Paper, 1804; https://dc.etsu.edu/etd/1804, 72 pages.

Smith et al., "$\Delta^1$-3-cis-Tetrahydrocannabinol in Cannabis Sativa," Phytochemistry, 16:1088-1089 (1977).

Thompson et al., "Oral and Intravenous Toxicity of $\Delta^9$-Tetrahydrocannabinol in Rheus Monkeys," Toxicology and Applied Pharmacology, 27:648-665 (1974).

Turkanis et al., "Excitatory and Depressant Effects of Delta-9-Tetrahydrocannabidinol and Cannabidiol on Cortical Evoked Responses in the Conscious Rat," Psychopharmacology, 75:294-298 (1981).

Vrielynck, P., "Current and emerging treatments for absence seizures in young patients," Neuropsychiatric Disease and Treatment, 9:963-975 (2013).

Weed Country, Episode 5, 2013; https://www.youtube.com/watch?v=0isjCcMtxBk; https://www.youtube.com/watch?v=GitMYGvwC4E&t=212s, 25 pages.

Weed Country, Episode 6, 2013; https://www.youtube.com/watch?v=Uyzuy1fNQfQ, 18 pages.

Wheless, J. W. et al., "Pharmacokinetics and Tolerability of Multiple Doses of Pharmaceutical-Grade Synthetic Cannabidiol in Pediatric Patients with Treatment-Resistant Epilepsy," CNS Drugs, 33(6):593-604 (2019); doi: 10.1007/s40263-019-00624-4.

Willis, L., "Final Report on the Safety Assessment of Sesame Oil," Journal of the American College of Toxicology, 12(3):261-277 (1993).

Zhang, T. et al., "Pre-seizure state identified by diffuse optical tomography," Scientific Reports, 4:3798 (2014); https://doi.org/10.1038/srep03798, 10 pages.

Zuardi et al., "Antipsychotic Effect of Cannabidiol," J Clin Psychiatry, 56(10):485-486 (1995).

Zuardi et al., "Cannabidiol for the treatment of psychosis in Parkinson's disease," Journal of Psychopharmacology, 23(8):979-983 (2009).

Bijnsdorp, I. V. et al., "Analysis of Drug Interactions," Chapter 34, Cancer Cell Culture, Methods in Molecular Biology, Second Edition, Ian A. Cree, Ed., 2011:731:421-34, 19 pages.

Chou, T.-C., "Drug Combination Studies and Their Synergy Quantification Using the Chou-Talalay Method," Cancer Res, 70(2):440-446 (2010).

FDA Guidance for Industry on Drug-Induced Liver Injury: Premarketing Clinical Evaluation, Food and Drug Administration, Jul. 30, 2009, 4 pages.

French, J. A. et al., "Adjunctive everolimus therapy for treatment-resistant focal-onset seizures associated with tuberous sclerosis (EXIST-3): a phase 3, randomised, double-blind, placebo-controlled study," Lancet, 388:2153-2163 (2016).

Gemmill, R. M. et al., "Synergistic growth inhibition by Iressa and Rapaymycin is modulated by VHL mutations in renal cell carcinoma," British Journal of Cancer, 92:2266-2277 (2005).

Kobayashi T., et al., "Renal Carcinogenesis, Hepatic Hemangiomatosis and Embryonic Lethality Caused by a Germ-Line Tsc2 Mutation in Mice," Cancer Research, 59:1206-1211 (1999).

Palmer, A. C. et al., "Combination Cancer Therapy Can Confer Benefit via Patient-to-Patient Variability without Drug Additivity or Synergy," Cell, 171:1678-1691 (2017).

Serra I., et al., "Cannabidiol modulates phosphorylated rpS6 signalling in a zebrafish model of Tuberous Sclerosis Complex," Behavioural Brain Research, 363:135-144 (2019).

Thomas et al., "Characterization of the Lipophilicity of Natural and Synthetic Analogs of 49. Tetrahydrocannabinol and Its Relationship to Pharmacological Potency," The Journal of Pharmacology and Experimental Therapeutics, 255(2):624-630 (1990).

Zuardi A., et al., "Inverted U-Shaped Dose-Response Curve of the Anxiolytic Effect of Cannabidiol during Public Speaking in Real Life," Frontiers in Pharmacology, 8, Article 259, pp. 1-9 (2017).

\* cited by examiner

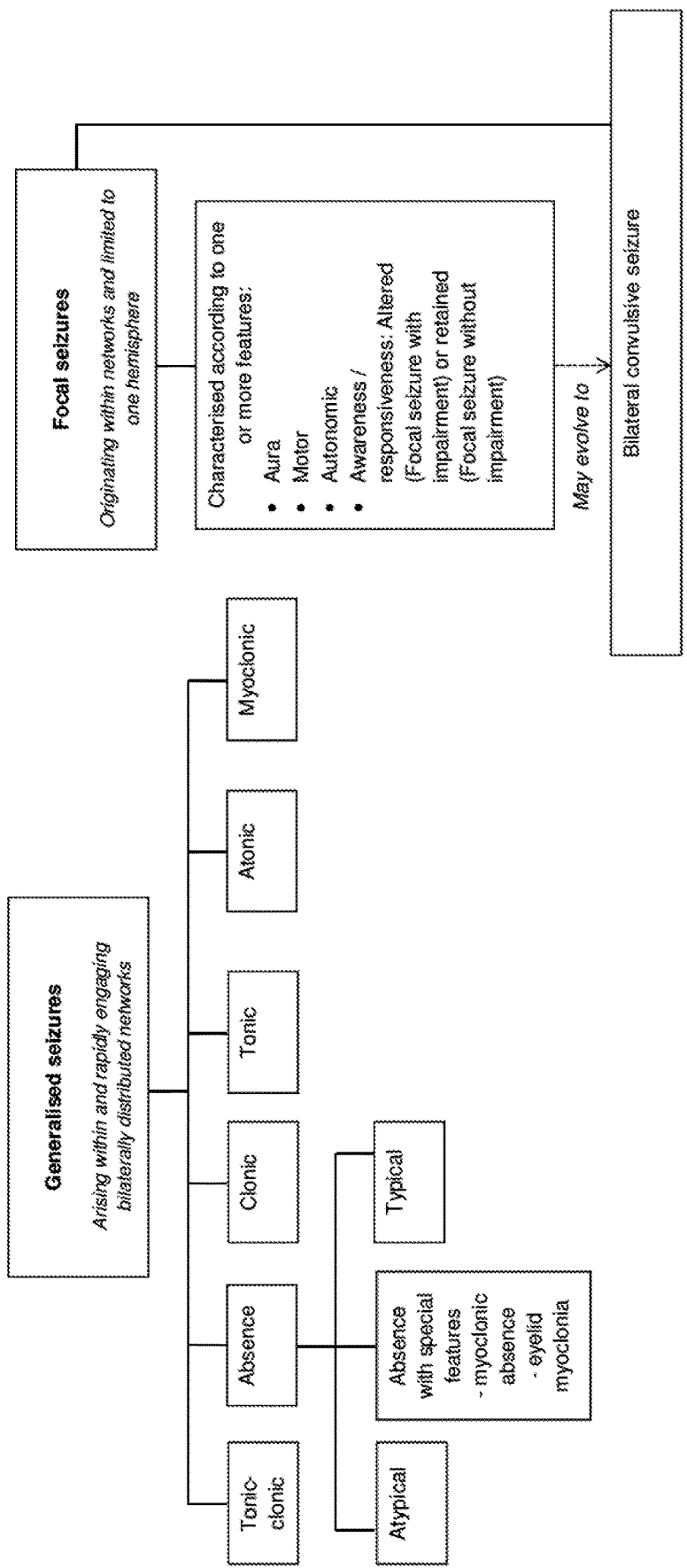

USE OF CANNABINOIDS IN THE TREATMENT OF EPILEPSY

CROSS-REFERENCE TO RELATED APPLICATIONS

This application is a continuation of U.S. patent application Ser. No. 16/893,018, filed Jun. 4, 2020, now U.S. Pat. No. 11,357,741, and which is a continuation of U.S. patent application Ser. No. 15/183,947, filed Jun. 16, 2016, now U.S. Pat. No. 10,709,671, and which claims priority to GB 1510664.4, filed Jun. 17, 2015. Each of these applications is incorporated herein by reference in its entirety.

FIELD OF THE INVENTION

The present invention relates to the use of cannabidiol (CBD) in the treatment of focal seizures. In one embodiment the patients suffering from focal seizures are children and young adults. CBD appears particularly effective in reducing focal seizures in patients suffering with etiologies that include: Lennox-Gastaut Syndrome; Tuberous Sclerosis Complex; Dravet Syndrome; CDKL5; Neuronal ceroid lipofuscinoses (NCL); febrile infection related epilepsy syndrome (FIRES); Aicardi syndrome and brain abnormalities in comparison to other seizure types.

Significantly GBD additionally is very effective in the reduction of a sub-type of focal seizures, focal seizures with impairment. The etiologies of patients which suffer from focal seizures with impairment include: Lennox-Gastaut Syndrome; Tuberous Sclerosis Complex; Dravet Syndrome; CDKL5; febrile infection related epilepsy syndrome (FIRES); Aicardi syndrome and brain abnormalities.

In these patients treatment with CBD reduced the occurrence of absence seizures or myoclonic absence seizures by greater than 50% in a large proportion of patients, 64% and 75% respectively. This was surprising given that the proportion of patients benefitting from a greater than 50% reduction in total seizures was significantly less, (46%), in all subjects treated.

Preferably the CBD used is in the form of a highly purified extract of *Cannabis* such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the GBD may be a synthetically produced CBD.

In use the CBD may be used concomitantly with one or more other anti-epileptic drugs (AED). Alternatively the CBD may be formulated for administration separately, sequentially or simultaneously with one or more AED or the combination may be provided in a single dosage form. Where the CBD is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et at, 2012), are unable to obtain seizure freedom using the AED that are available and as such are termed as suffering from intractable or "treatment-resistant epilepsy" (TIRE).

Intractable or treatment-resistant epilepsy was defined in 2009 by the International League Against Epilepsy (ILAE) as "failure of adequate trials of two tolerated and appropriately chosen and used RED schedules (whether as monotherapies or in combination) to achieve sustained seizure freedom" (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from, an investigation into the type of seizures that the patient is experiencing is undertaken. Clinical observations and electroencephalography (EEG) tests are conducted and the type(s) of seizures are classified according to the ILAE classification described below and in FIG. 1.

The International classification of seizure types proposed by the ILAE was adopted in 1981 and a revised proposal was published by the ILAE in 2010 and has not yet superseded the 1981 classification. FIG. 1 is adapted from the 2010 proposal for revised terminology and includes the proposed changes to replace the terminology of partial with focal, In addition the term "simple partial seizure" has been replaced by the term "focal seizure where awareness/responsiveness is not impaired" and the term "complex partial seizure" has been replaced by the term "focal seizure where awareness/consciousness is impaired".

From FIG. 1 it can be seen that Generalised seizures, where the seizure arises within and rapidly engages bilaterally distributed networks, can be split into six subtypes: Tonic-Clonic (grand mal) seizures; Absence (petit mal) Seizures; Clonic Seizures; Tonic Seizures; Atonic Seizures and Myoclonic Seizures.

Focal (partial) seizures where the seizure originates within networks limited to only one hemisphere, are also split into sub-categories. Here the seizure is characterized according to one or more features of the seizure, including aura, motor, autonomic and awareness responsiveness. Where a seizure begins as a localized seizure and rapidly evolves to be distributed within bilateral networks this seizure is known as a Bilateral convulsive seizure, which is the proposed terminology to replace Secondary Generalized Seizures (generalized seizures that have evolved from focal seizures and are no longer remain localized).

Focal seizures where the subjects awareness/responsiveness is altered are referred to as focal seizures with impairment and focal seizures where the awareness or responsiveness of the subject is not impaired are referred to as focal seizures without impairment.

Focal seizures may occur in epilepsy syndromes including: Lennox-Gastaut Syndrome; Tuberous Sclerosis Complex; Dravet Syndrome; CDKL5: Neuronal ceroid lipofuscinoses (NCL); febrile infection related epilepsy syndrome (FIRES); Aicardi syndrome and brain abnormalities.

Epileptic syndromes often present with many different types of seizure and identifying the types of seizure that a patient is suffering from is important as many of the standard AED's are targeted to treat or are only effective against a given seizure type/sub-type.

One such childhood epilepsy is Dravet syndrome. Onset of Dravet syndrome almost always occurs during the first year of life with clonic and tonic-clonic seizures in previously healthy and developmentally normal infants (Dravet, 2011). Symptoms peak at about five months of age. Other seizures develop between one and four years of age such as prolonged focal dyscognitive seizures and brief absence seizures.

In diagnosing Dravet syndrome both focal and generalised seizures are considered to be mandatory, Dravet patients may also experience atypical absence seizures, myoclonic absence seizures, atonic seizures and non-convulsive status epilepticus.

Seizures progress to be frequent and treatment-resistant, meaning that the seizures do not respond well to treatment. They also tend to be prolonged, lasting more than 5 minutes. Prolonged seizures may lead to status epilepticus, which is a seizure that lasts more than 30 minutes, or seizures that occur in clusters, one after another.

Prognosis is poor and approximately 14% of children die during a seizure, because of infection, or suddenly due to uncertain causes, often because of the relentless neurological decline. Patients develop intellectual disability and lifelong ongoing seizures. Intellectual impairment varies from severe in 50% patients, to moderate and mild intellectual disability each accounting for 25% of cases.

There are currently no FDA approved treatments specifically indicated for Dravet syndrome. The standard of care usually involves a combination of the following anticonvulsants: clobazam, clonazepam, levetiracetam, topiramate and valproic acid.

Stiripentol is approved in Europe for the treatment of Dravet syndrome in conjunction with clobazam and valproic acid. In the US, stiripentol was granted an Orphan Designation for the treatment of Dravet syndrome in 2008; however, the drug is not FDA approved.

Potent sodium channel blockers used to treat epilepsy actually increase seizure frequency in patients with Dravet Syndrome. The most common are phenytoin, carbamazepine, lamotrigine and rufinamide.

Management may also include a ketogenic diet, and physical and vagus nerve stimulation. In addition to anticonvulsive drugs, many patients with Dravet syndrome are treated with anti-psychotic drugs, stimulants, and drugs to treat insomnia.

The first line treatment for focal seizures are AED such as carbamezapine or lamotrigine. Levetiracetam, oxycarbamezapine or sodium valproate are also considered to be of use. A combination of these medicaments may be required in order to treat focal seizures.

Common AED defined by their mechanisms of action are described in the following tables:

TABLE 1

Examples of narrow spectrum AED

| Narrow-spectrum AED | Mechanism | Indication |
|---|---|---|
| Phenytoin | Sodium channel | Complex partial<br>Tonic-clonic |
| Phenobarbital | GABA/Calcium channel | Partial seizures<br>Tonic-clonic |
| Carbamazepine | Sodium channel | Partial seizures<br>Tonic-clonic<br>Mixed seizures |
| Oxcarbazepine | Sodium channel | Partial seizures<br>Tonic-clonic<br>Mixed seizures |
| Gabapentin | Calcium channel | Partial seizures<br>Mixed seizures |
| Pregabalin | Calcium channel | Adjunct therapy for partial seizures with or without secondary generalisation |
| Lacosamide | Sodium channel | Adjunct therapy for partial seizures |
| Vigabatrin | GABA | Secondarily generalized tonic-clonic seizures<br>Partial seizures<br>Infantile spasms due to West syndrome |

TABLE 2

Examples of broad spectrum AED

| Broad-spectrum AED | Mechanism | Indication |
|---|---|---|
| Valproic acid | GABA/Sodium channel | First-line treatment for tonic-clonic seizures, absence seizures and myoclonic seizures<br>Second-line treatment for partial seizures and infantile spasms.<br>Intravenous use in status epilepticus |
| Lamotrigine | Sodium channel | Partial seizures<br>Tonic-clonic<br>Seizures associated with Lennox-Gastaut syndrome |
| Ethosuximide | Calcium channel | Absence seizures |
| Topiramate | GABA/Sodium channel | Seizures associated with Lennox-Gastaut syndrome |
| Zonisamide | GABA/Calcium/Sodium channel | Adjunctive therapy in adults with partial-onset seizures<br>Infantile spasm<br>Mixed seizure<br>Lennox-Gastaut syndrome<br>Myoclonic<br>Generalised tonic-clonic seizure |
| Levetiracetam | Calcium channel | Partial seizures<br>Adjunctive therapy for partial, myoclonic and tonic-clonic seizures |
| Clonazepam | GABA | Typical and atypical absences<br>Infantile myoclonic<br>Myoclonic seizures<br>Akinetic seizures |
| Rufinamide | Sodium channel | Adjunctive treatment of partial seizures associated with Lennox-Gastaut syndrome |

TABLE 3

Examples of AED used specifically in childhood epilepsy

| AED | Mechanism | Indication |
| --- | --- | --- |
| Clobazam | GABA | Adjunctive therapy in complex partial seizures<br>Status epilepticus<br>Myoclonic<br>Myoclonic-absent<br>Simple partial<br>Complex partial<br>Absence seizures<br>Lennox-Gastaut syndrome |
| Stiripentol | GABA | Severe myoclonic epilepsy in infancy (Dravet syndrome) |

From these tables it can be seen that there are many AED are approved for use in focal (partial) seizures which work by a different mechanisms. Indeed the only AED that has been approved for use in the treatment of complex partial seizures (focal seizures with impairment) is the AED phenytoin.

Over the past forty years there have been a number of animal studies on the use of the non-psychoactive cannabinoid cannabidiol (CBD) to treat seizures. For example, Consroe of (1982) determined that GBD was able to prevent seizures in mice after administration of pro-convulsant drugs or an electric current.

Studies in epileptic adults have also occurred in the past forty years with CBD, Cunha et al. reported that administration of CBD to eight adult patients with generalized epilepsy resulted in a marked reduction of seizures in 4 of the patients (Cunha of al., 1980).

A study in 1978 provided 200 mg/day of pure CBD to four adult patients, two of the four patients became seizure free, whereas in the remainder seizure frequency was unchanged (Mechoulam and Carlini, 1978).

In contrast to the studies described above, an open label study reported that 200 mg day of pure CBD was ineffective in controlling seizures in twelve institutionalized adult patients (Ames and Gridland, 1986).

Based on the fact that chronologically the last study to look at the effectiveness of CBD in patients with epilepsy proved that CBD was unable to control seizures, there would be no expectation that CBD might be useful as an anti-convulsant agent.

In the past forty years of research there have been over thirty drugs approved for the treatment of epilepsy none of which are cannabinoids. Indeed, there appears to have been a prejudice against cannabinoids, possibly due to the scheduled nature of these compounds and/or the fact that THC, which is a known psychoactive, has been ascribed as a pro-convulsant (Consroe of al., 1977).

A paper published recently suggested that cannabidiol-enriched *Cannabis* may be efficacious in the treatment of epilepsy. Porter and Jacobson (2013) report on a parent survey conducted via a Facebook group which explored the use of *Cannabis* which was enriched with CBD in children with treatment-resistant epilepsy. It was found that sixteen of the 19 parents surveyed reported an improvement in their child's epilepsy. The children surveyed for this paper were all taking *Cannabis* that was purported to contain CBD in a high concentration although the amount of CBD present and the other constituents including THC were not known for many of the cases, Indeed, whilst CBD levels ranged from 0.5 to 28.6 mg/kg/day (in those extracts tested), THC levels as high as 0.8 mg/kg/day were reported.

Providing children with TIRE with a *Cannabis* extract that comprises THC, which has been described as a pro-convulsant (Consroe et al., 1977), at a potentially psychoactive dose of 0.8 mg/kg/day, is a concern and as such there is a need to determine whether CBD is in fact efficacious.

In November 2013 the company OW Pharmaceuticals made a press release to state that they were intending to treat Dravet Syndrome with CBD as it had received orphan drug designation. A further press release was made in June 2014 which stated promising signals of efficacy in children with treatment-resistant epilepsy, including patients with Dravet syndrome.

The international patent application WO 2015/193667 describes the use of CBD in treatment resistant epilepsy. Patients included nine with Dravet syndrome out of 27 others.

The international patent application WO 2015/193668 describes the use of CBD in the treatment of absence seizures, Patients included those with Dravet syndrome in addition to ten other syndromes.

Maa and Figi (2014) discuss the case for medical marijuana in epilepsy and discuss the positive treatment of a girl Charlotte with Dravet syndrome who experienced frequent bouts of febrile and afebrile status epilepticus as well as tonic, tonic-clonic and myoclonic seizures (generalised seizures). She was given an extract from a *Cannabis* plant dubbed "Charlotte's Web" which according to the suppliers, CW Botanicals, disclose that their extracts are rich in terpenes and contain from 10 to 200 times the amount found in other proprietary plants. In other words the suggestion is that the efficacy is based on a combination of CBD and the terpenes present in their extracts.

Press et al. (3 Apr. 2015), provides an in depth review of the parental reporting of pediatric patients with refractory epilepsy that were given oral *Cannabis* extracts (OCE). Despite it's in depth nature it concludes no studies demonstrate clear efficacy.

Significantly the document recognizes the effectiveness of an anti-seizure medication may be dependent upon: the drug itself, including CBD, (see Table 3); the epilepsy syndrome type (Table 2); and the seizure type (Table 2).

Very significantly the document in the discussion recognises caution needs to be taken when reviewing, particularly open label study data, since placebo rates may be high. Indeed it specifically comments that "four recently FDA approved anti-convulsant medications had placebo rates of 31.6%, 26.4%, 20% and 21% respectively" (page 51, left hand column).

Furthermore the analysis observed a surprising finding namely that "new residents of Colorado (those moving to obtain treatment) were more than three times as likely to report a greater than 50% seizure reduction than families with established care in Colorado" suggestive that studies such as that published in Porter and Jacobson (2013) may be highly flawed.

The skilled person would infer therefore from Press et al. would be that the drug type CBD plus the presence of "other OCE" (such as, other cannabinoids most likely THC and non-cannabinoids such as e.g. terpenes) appears a more interesting combination than CBD alone—responder rate 63% versus 35%.

That the epilepsy syndrome Lennox-Gastaut appears the most promising target with 89% responder rate versus Dravet (23% responder rate) or Doose (0% responder rate).

That of the seizure types studied ranged from 44% responder rate for atonic seizures to 17% responder rates in tonic seizures, amongst the seven seizures types reviewed.

The assessment looked at three distinct groups, namely; the OCE type, Table 3 (four OCE types); the epilepsy syndrome, see for example, page 50 right hand column line 3 (three syndrome types); and the seizure type, see page 51, Table 2 (seven seizure types).

In all this provides the reader with information on 84 different alternative combinations.

The problem facing the skilled practitioner looking at *Cannabis* medicines in the field of epilepsy where many patients are refractory to existing medications is to select the appropriate cannabinoid and its form targeted to a given seizure type in a given patient group.

Perhaps therefore it is not surprising that in the Cochrane report (Gloss and Vickrey) published March 2014 undertook a full review on the efficacy of cannabinoids in the treatment of epilepsy concluded "no reliable conclusions can be drawn at present regarding the efficacy of cannabinoids as a treatment for epilepsy."

Surprisingly the applicant has shown that CBD is particularly effective in the treatment of focal seizures in Dravet syndrome patients, particularly children and more particularly those which are resistant to existing treatments.

BRIEF SUMMARY OF THE DISCLOSURE

In accordance with a first aspect of the present invention there is provided Cannabidiol (CBD) for use in the treatment of focal seizures in Dravet Syndrome.

In one embodiment the focal seizures are focal seizures with impairment.

Preferably the Dravet Syndrome is treatment-resistant.

In a further embodiment the CBD is for use in combination with one or more concomitant anti-epileptic drugs (AED).

In a further embodiment the CBD is present as a highly purified extract of *Cannabis* which comprises at least 98% (w/w) CBD. Preferably the extract comprises less than 0.15% THC. More preferably the extract further comprises up to 1% CBDV.

In an alternative embodiment the CBD is present as a synthetic compound.

In a further embodiment of the invention the one or more AED is selected from the group consisting of: carbamezapine, clobazam, clonazepam, clonidine, clorazepate, desmethylclobazam, diazepam, ethosuximide, felbamate, ketogenic diet, lacosamide, lamotrigine, levetiracetam, lorazepam, midazolam, N-desmethylciobazam, nordiazepam, oxycarbamezapine, perampanel, phenobarbital, phenytoin, pregabalin, rufinamide, stiripentol, topiramate, trazodone, vagus nerve stimulation, valproic acid, vigabatrin, and zonisamide.

Preferably the number of different anti-epileptic drugs that are used in combination with the GBD is reduced. Alternatively the dose of anti-epileptic drugs that are used in combination with the CBD is reduced.

There are many side effects associated with the commonly used AED which include dizziness, blurred vision, nausea, respiratory system depression, tiredness, headaches, and other motor side effects on the central nervous system. These side effects are particularly common as higher doses or combinations of numerous AED are used. As such there is a need for an alternative medication that is able to reduce the numbers of seizures whilst at the same time exhibiting a safe side effect profile.

Preferably the dose of CBD is greater than 5 mg/kg/day. Thus for a 15 kg patient a dose of greater than 75 mg of CBD per day would be provided. Doses greater than 5 mg/kg/day such as greater than 10/mg/day, greater than 15 mg/kg/day, greater than 20 mg/kg/day and greater than 25 mg/kg/day are also envisaged to be effective.

In accordance with a second aspect of the present invention there is provided a method of treating focal seizures in Dravet Syndrome comprising administering cannabidiol (CBD) to a subject.

Preferably the subject is a human.

In accordance with a third aspect of the present invention there is provided a composition for use in the treatment of epilepsy characterised by focal seizures in Dravet syndrome comprising cannabidiol (CBD), a solvent, a co-solvent, a sweetener, and a flavouring.

Preferably the solvent is sesame oil, the co-solvent is ethanol, the sweetener is sucralose, the flavouring is strawberry flavour and the CBD is present at a concentration of between 25 mg/ml and 100 mg/ml, namely 50 mg/ml and 75 mg/ml.

More preferably the composition comprises cannabidiol (CBD) at a concentration of between 25 to 100 mg/ml, ethanol at a concentration of 79 mg/ml, sucralose at a concentration of 0.5 mg/ml, strawberry flavouring at a concentration of 0.2 mg/ml and sesame oil q.s. to 1.0 ml.

It is envisaged that the composition be administered as an oral liquid solution. Other modes of administration including solids, semi-solids, gels, sprays, aerosols, inhalers, vaporisers, enemas and suppositories are alternative administration forms. Such medicaments could be administered via the oral, buccal, sublingual, respiratory nasal and distal rectum route.

Definitions

Definitions of some of the terms used to describe the invention are detailed below:

The cannabinoids described in the present application are listed below along with their standard abbreviations.

TABLE 4

Cannabinoids and their abbreviations

CBD     Cannabidiol

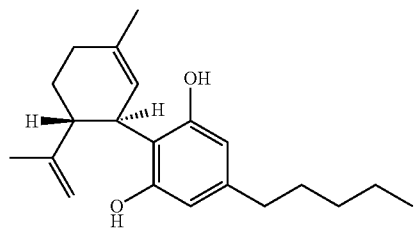 [SMILES: C=C(C)[C@@H]1CCC(C)=C[C@H]1c1c(O)cc(CCCCC)cc1O]

TABLE 4-continued

Cannabinoids and their abbreviations

CBDA  Cannabidiolic acid

CBDV  Cannabidivarin

CBDVA  Cannabidivarinic acid

THC  Tetrahydrocannabinol

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *Cannabis* plant. The phytocannabinoids can be isolated from plants to produce a highly purified extract or can be reproduced synthetically.

"Highly purified cannabinoid extracts" are defined as cannabinoids that have been extracted from the *Cannabis* plant and purified to the extent that other cannabinoids and non-cannabinoid components that are co-extracted with the cannabinoids have been substantially removed, such that the highly purified cannabinoid is greater than or equal to 98% (why) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Treatment-resistant epilepsy" (IRE) or "intractable epilepsy" is defined as per the ILAE guidance of 2009 as epilepsy that is not adequately controlled by trials of one or more RED.

"Childhood epilepsy" refers to the many different syndromes and genetic mutations that can occur to cause epilepsy in childhood. Examples of some of these are as follows: Dravet Syndrome; Myoclonic-Absence Epilepsy: Lennox-Gastaut syndrome; Generalized Epilepsy of unknown origin; CDKL5 mutation; Aicardi syndrome; bilateral polymicrogyria; Dup15q: SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

"Focal Seizures" are defined as seizures which originate within networks limited to only one hemisphere. What happens during the seizure depends on where in the brain the seizure happens and what that part of the brain normally does.

"Focal seizure where awareness/consciousness are impaired" has replaced the term "complex partial seizure".

These seizures usually start in a small area of the temporal lobe or frontal lobe of the brain and involve other areas of the brain within the same hemisphere that affect alertness and awareness. Most subjects experience automatisms during a focal seizure with impaired consciousness.

"Mixed seizures" are defined as the existence of both generalised and focal seizures in the same patient.

The terms "50% responder" and "50% reduction in seizure" are both terms used in clinical studies. In the present application the terms define the percentage of subjects that experienced a greater than or equal to 50% reduction in the number of seizures during treatment with CBD in comparison to the number experienced during the baseline period before the CBD was administered.

DETAILED DESCRIPTION

Preparation of Highly Purified CBD Extract

The following describes the production of the highly-purified (>98% w/w) cannabidiol extract which has a known and constant composition which was used for the expanded access trials described in the Examples below.

In summary the drug substance used in the trials is a liquid carbon dioxide extract of high-CBD containing chemotypes of *Cannabis sativa* L which had been further purified by a solvent crystallization method to yield CBD. The crystallisation process specifically removes other cannabinoids and plant components to yield greater than 98% CBD.

The *Cannabis sativa* L plants are grown, harvested, and processed to produce a botanical extract (intermediate) and then purified by crystallization to yield the CBD (drug substance).

The plant starting material is referred to as Botanical Raw Material (BRM); the botanical extract is the intermediate; and the active pharmaceutical ingredient (API) is CBD, the drug substance.

Both the botanical starting material and the botanical extract are controlled by specifications. The drug substance specification is described in Table 1 below.

TABLE 5

| CBD Specification | | |
|---|---|---|
| Test | Test Method | Limits |
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| Other Cannabinoids: | HPLC-UV | |
| CBDA | | NMT 0.15% w/w |
| CBDV | | NMT 1.0% w/w |
| $\Delta^9$ THC | | NMT 0.15% w/w |
| CBD-C4 | | NMT 0.5% w/w |

TABLE 5-continued

| CBD Specification | | |
|---|---|---|
| Test | Test Method | Limits |
| Residual Solvents: | GC | |
| Alkane | | NMT 0.5% w/w |
| Ethanol | | NMT 0.5% w/w |
| Residual Water | Karl Fischer | NMT 1.0% w/w |

NMT—Not more than

The purity of the CBD drug substance achieved is greater than 98%. The other cannabinoids which may occur in the extract are: CBDA, CBDV, CBD-C4 and THC.

Distinct chemotypes of *Cannabis sativa* L plant have been produced to maximize the output of the specific chemical constituents, the cannabinoids. One type of plant produces predominantly CBD. Only the (−)-trans isomer occurs naturally. Furthermore during purification the stereochemistry of CBD is not affected.

Production of the Intermediate

An overview of the steps to produce a botanical extract, the intermediate, are as follows:
1. Growing
2. Decarboxylation
3. Extraction No. 1—using liquid $CO_2$
4. Extraction No. 2—'winterization' using ethanol
5. Filtration
6. Evaporation High CBD chemovars were grown, harvested and dried and stored in a dry room until required. The botanical raw material (BRM) was finely chopped using an Apex mill fitted with a 1 mm screen. The milled BRM was stored in a freezer for up to 3 months prior to extraction.

Decarboxylation of CBDA to CBD was carried out using a large Heraeus tray oven. The decarboxylation batch size in the Heraeus is approximately 15 Kg. Trays were placed in the oven and heated to 105° C.; the BRM took 96.25 minutes to reach 105° C. Held at 105° C. for 15 Minutes. Oven then set to 150° C.; the BRM took 75.7 minutes to reach 150° C.; BRM held at 150° C. for 130 Minutes. Total time in the oven was 380 Minutes, including 45 minutes cooling and 15 Minutes venting.

Extraction No 1 was performed using liquid $CO_2$ at 60 bar/10° C. to produce botanical drug substance (BIDS).

The crude CBD BDS was winterised in Extraction No 2 under standard conditions (2 volumes of ethanol at minus 20° C. for around 50 hours). The precipitated waxes were removed by filtration and the solvent evaporated using the rotary evaporator (water bath up to 60° C.) to yield the BDS, which was then used for crystallisation to produce the test material.

Production of the Drug Substance

The manufacturing steps to produce the drug substance from the intermediate botanical extract are as follows:
1. Crystallization using C5-C12 straight chain or branched alkane
2. Filtration
3. Optional recrystallization from C5-C12 straight chain or branched alkane
4. Vacuum drying Intermediate botanical extract (12 kg) produced using the methodology above was dispersed in C5-C12 straight chain or branched alkane (9000 ml, 0.75 vols) in a 30 litre stainless steel vessel.

The mixture was manually agitated to break up any lumps and the sealed container then placed in a freezer for approximately 48 hours.

The crystals were isolated by vacuum filtration, washed with aliquots of cold C5-C12 straight chain or branched alkane (total 12000 ml), and dried under a vacuum of <10 mb at a temperature of 60 until dry before submitting the drug substance for analysis.

The dried product was stored in a freezer at minus 20° C. in a pharmaceutical grade stainless steel container, with FDA food grade approved silicone seal and clamps.

Production of the Drug Product

The drug product is presented as an oral solution. The oral solution presentation contains 25 mg/ml or 100 mg/ml CBD, with the excipients sesame oil, ethanol, sucralose and flavouring. Two product strengths are available to allow dose titration across a wide dose range.

The 25 mg/ml solution is appropriate at lower doses and the 100 mg/ml solution at higher doses.

The drug product formulation is as described in Table 6 below:

TABLE 6

Drug Product specification

| Component | Qualitative Composition | Function | Reference to Quality Standard |
|---|---|---|---|
| Cannabidiol (CBD) | 25 mg/ml or 100 mg/ml | Active | In-house |
| Anhydrous ethanol | 79.0 mg/ml* | Excipient | Ph. Eur. |
| Sucralose | 0.5 mg/ml | Sweetener | In-house |
| Strawberry flavouring | 0.2 mg/ml | Flavouring | In-house |
| Sesame oil | q.s to 1.0 ml | Excipient | Ph. Eur. |

The drug substance. CBD is insoluble in water. Sesame oil was selected as an excipient to solubilize the drug substance.

A sweetener and fruit flavouring are required to improve palatability of the sesame oil solution.

Ethanol was required to solubilize the sweetener and the flavouring.

The composition can be substantially equivalent, by which is meant the functional ingredients can vary from the qualitative composition specified in Table 6 by an amount of up to 10%.

Example 1 below describes the use of a highly purified *Cannabis* extract comprising cannabidiol (CBD). Cannabidiol is the most abundant non-psychoactive cannabinoid in the selected chemovar. Previous studies in animals have demonstrated that GBD has anticonvulsant efficacy in multiple species and models.

Example 1 describes data produced in an expanded access treatment program in children with TRE.

Example 1: Efficacy of Cannabidiol Reducing Focal Seizures in Children and Young Adults with Intractable Epilepsy Materials and Methods Of 137 children and young adults with severe, childhood onset treatment-resistant epilepsy (TRE), fifty-one suffered from epilepsy that was characterised by focal seizures. These subjects were tested with a highly purified extract of cannabidiol (CBD) obtained from a *Cannabis* plant. All subjects presented with focal type seizures, often in addition to generalised seizures. The participants in the study were part of an expanded access compassionate use program for CBD.

The epileptic syndromes that these patients suffered from were as follows: Lennox-Gastaut Syndrome; Tuberous Sclerosis Complex; Dravet Syndrome; CDKL5; Neuronal ceroid lipofuscinoses (NCL); febrile infection related epilepsy syndrome (FIRES); Aicardi syndrome and brain abnormalities.

Other seizure types experienced by these patients included: tonic, clonic, tonic-clonic, myoclonic, atonic, absence, myoclonic-absence, focal seizures without impairment, focal seizures with impairment and focal seizures evolving to bilateral convulsive seizures.

All patients entered a baseline period of 4 weeks when parents/caregivers kept prospective seizure diaries, noting all countable seizure types.

The patients then received a highly purified CBD extract (greater than 98% CBD w/w) in sesame oil, of known and constant composition, at a dose of 5 mg/kg/day in addition to their baseline anti-epileptic drug (AED) regimen.

The daily dose was gradually increased by 2 to 5 mg/kg increments until intolerance occurred or a maximum dose of 25 mg/kg/day was achieved.

Patients were seen at regular intervals of 2-4 weeks. Laboratory testing for hematologic, liver, kidney function and concomitant AED levels was performed at baseline, and after every 4 weeks of CBD therapy.

The patients on the study were all taking at least one concomitant AED. These included: carbamezapine, clobazam, clonazepam, clonidine, clorazepate, desmethylclobazam, diazepam, ethosuximide, felbamate, ketogenic diet, lacosamide, lamotrigine, levetiracetam, lorazepam, midazolam, N-desmethylclobazam, nordiazepam, oxycarbamezapine, perampanel, phenobarbital, phenytoin, pregabalin, rufinamide, stiripentol, topiramate, trazodone, vagus nerve stimulation, valproic acid, vigabatrin, and zonisamide.

Results

The 51 children and young adult patients ail of whom suffered from focal seizures received treatment with CBD who received treatment for at least 12 weeks.

A summary of the 50% responders, based on 12 weeks of treatment are summarized in Table 7 below.

TABLE 7

Summary of 50% responders after 12 weeks of treatment for focal seizures

| | Focal seizures (n = 51) | Total seizures (n = 137) |
|---|---|---|
| >50% reduction in seizures | 63% (n = 32) | 46% (n = 63) |
| <50% reduction in seizures | 37% (n = 19) | 54% (n = 74) |

Table 7 shows that after 3 months of therapy, a remarkable 63% of patients had an equal to or greater than >50% reduction in focal seizures, these data infer that the CBD is very effective at reducing this type of seizure.

Conclusions

These data indicate that CBO significantly reduces the number of focal seizures in a high proportion of patients that do not respond well to existing AED.

It was surprising that in this group of patients which are treatment-resistant such a high number were able to gain an effect. The fact that nearly two thirds of the patients (63%)

benefitted from at least a fifty percent reduction in the number of focal seizures that they suffered from was remarkable.

Example 2: Efficacy of Cannabidiol Reducing Focal Seizures with Impairment in Children and Young Adults with Intractable Epilepsy Materials and Methods Of 137 children and young adults with severe, childhood onset treatment-resistant epilepsy (TRE), thirty-seven suffered from epilepsy that was characterised by focal seizures with impairment. These subjects were tested with a highly purified extract of cannabidiol (CBD) obtained from a *Cannabis* plant. All subjects presented with focal seizures with impairment, often in addition to other generalised and/or focal seizures. The participants in the study were part of an expanded access compassionate use program for CBD.

The epileptic syndromes that these patients suffered from were as follows: Lennox-Gastaut Syndrome; Tuberous Sclerosis Complex; Dravet Syndrome; CDKL5; febrile infection related epilepsy syndrome (FIRES); Aicardi syndrome and brain abnormalities.

All patients entered a baseline period of 4 weeks when parents/caregivers kept prospective seizure diaries, noting all countable seizure types.

The patients then received a highly purified CBD extract (greater than 98% CBD w/w) in sesame oil, of known and constant composition, at a dose of 5 mg/kg/day in addition to their baseline anti-epileptic drug (AED) regimen.

The daily dose was gradually increased by 2 to 5 mg/kg increments until intolerance occurred or a maximum dose of 25 mg/kg/day was achieved.

Patients were seen at regular intervals of 2-4 weeks. Laboratory testing for hematologic, liver, kidney function and concomitant AED levels was performed at baseline, and after every 4 weeks of CBD therapy.

The patients on the study were all taking at least one concomitant AED. These included: carbamezapine, clobazam, clonazepam, clorazepate, desmethylclobazam, diazepam, ethosuximide, felbamate, ketogenic diet, lacosamide, lamotrigine, levetiracetam, lorazepam, midazolam. N-desmethylclobazam, nordiazepam, oxycarbamezapine, perampanel, phenobarbital, phenytoin, pregabalin, rufinamide, topiramate, vagus nerve stimulation, valproic acid, vigabatrin, and zonisamide.

Results

The 37 children and young adult patients all of whom suffered from focal seizures with impairment received treatment with CBD who received treatment for at least 12 weeks.

A summary of the 50% responders, based on 12 weeks of treatment are summarized in Table 8 below.

TABLE 8

Summary of 50% responders after 12 weeks of treatment for focal seizures with impairment

|  | Focal Seizures with Impairment (n = 37) | Total seizures (n = 137) |
| --- | --- | --- |
| >50% reduction in seizures | 65% (n = 24) | 46% (n = 63) |
| <50% reduction in seizures | 35% (n = 13) | 54% (n = 74) |

Table 8 shows that after 3 months of therapy, a remarkable 65% of patients had an equal to or greater than >50% reduction in focal seizures with impairment, these data infer that the CBD is very effective at reducing this type of seizure.

Furthermore when these data are compared to the other sub-types of focal seizure, namely focal seizure without impairment and focal seizures leading to secondary generalisation it can clearly be seen that CBD was able to selectively reduce the occurrence of focal seizures with impairment. Table 9 below details these findings.

TABLE 9

Summary of 50% responders after 12 weeks of treatment for all focal seizure types

|  | Focal Seizures with Impairment (n = 37) | Focal Seizures without Impairment (n = 6) | Focal Seizures Leading to Secondary Generalised (n = 15) | Total Focal seizures (n = 51) |
| --- | --- | --- | --- | --- |
| >50% reduction in seizures | 65% (n = 24) | 50% (n = 3) | 47% (n = 7) | 63% (n = 32) |
| <50% reduction in seizures | 35% (n = 13) | 50% (n = 3) | 53% (n = 8) | 37% (n = 19) |

Conclusions

These data indicate that CBD significantly reduces the number of focal seizures with impairment in a selective manner.

It was surprising that in this group of patients which are treatment-resistant such a high number were able to gain an effect. The fact that over two thirds of the patients (65%) benefitted from at least a fifty percent reduction in the number of focal seizures with impairment that they suffered from was remarkable.

REFERENCES

Ames F R and Cridland S (1986). "Anticonvulsant effects of cannabidiol." S Afr Med J 69:14.

Consroe P, Martin P, Eisenstein D. (1977). "Anticonvulsant drug antagonism of delta-9-tetrahydrocannabinol induced seizures in rabbits." Res Commun Chem Pathol Pharmacol. 16:1-13

Consroe P, Benedicto M A, Leite J R, Carlini E A, Mechoulam R. (1982). "Effects of cannabidiol on behavioural seizures caused by convulsant drugs or current in mice." Eur J Pharmaco. 83: 293-8

Cunha J M, Carlini E A, Pereira A E, Ramos O L, Pimental C, Gagliardi R et al. (1980), "Chronic administration of cannabidiol to healthy volunteers and epileptic patient." Pharmacology. 21:175-85

Dravet C. The core Dravet syndrome phenotype. Epilepsia. 2011 April; 52 Suppl 2:3-9.

Eadie, M J (December 2012), "Shortcomings in the current treatment of epilepsy." *Expert Review of Neurotherapeutics* 12 (12): 1419-27.

Kwan P, Arzimanoglou A, Berg A T, Brodie M J, Hauser W A, Mathern G, Moshé S L, Perucca E, Wiebe S, French J. (2009) "Definition of drug resistant epilepsy: Consensus proposal by the ad hoc Task Force of the ILAE Commission on Therapeutic Strategies." *Epilepsia*.

Mechoulam R and Carlini E A (1978). "Toward drugs derived from *Cannabis*." Die naturwissenschaften 65:174-9.

Porter B E, Jacobson C (December 2013). "Report of a parent survey of cannabidiol-enriched *Cannabis* use in paediatric treatment resistant epilepsy" Epilepsy Behaviour. 29(3) 574-7

Thurman, D J; Beghi, E; Begley, C E; Berg, A T; Buchhalter, J R; Ding, D; Hesdorffer, D C; Hauser, W A; Kazis, L; Kobau, R; Kroner, B; Labiner, D; Liow, K; Logroscino, G; Medina, M T; Newton, C R; Parko, K; Paschal, A; Preux, P M: Sander, J W; Selassie, A; Theodore, W;

Tomson, T; Wiebe, S; ILAE Commission on, Epidemiology (September 2011). "Standards for epidemiologic studies and surveillance of epilepsy." *Epilepsia*. 52 Suppl 7: 2-26

The invention claimed is:

1. A method of treating focal seizures in Lennox-Gastaut Syndrome or Tuberous Sclerosis Complex, comprising administering to a subject in need thereof a drug product comprising a cannabidiol (CBD) drug substance, wherein the CBD drug substance has a purity of at least 98% (w/w), wherein the CBD is administered at a dose ranging from about 5 mg/kg/day to about 25 mg/kg/day.

2. The method of claim 1, wherein the focal seizures are focal seizures with impairment.

3. The method of claim 1, wherein the Lennox-Gastaut Syndrome or Tuberous Sclerosis Complex is treatment-resistant.

4. The method of claim 1, wherein the CBD is administered in combination with one or more concomitant anti-epileptic drugs (AED).

5. The method of claim 1, wherein the CBD is a highly purified extract of *Cannabis*.

6. The method of claim 5, wherein the highly purified extract further comprises less than 0.15% tetrahydrocannabinol (THC).

7. The method of claim 5, wherein the highly purified extract further comprises up to 1% (w/w) cannabidivarin (CBDV).

8. The method of claim 1, wherein the CBD is present as a synthetic compound.

9. The method of claim 4, wherein the one or more AED is selected from the group consisting of: carbamezapine, clobazam, clonazepam, clonidine, clorazepate, desmethylclobazam, diazepam, ethosuximide, felbamate, ketogenic diet, lacosamide, lamotrigine, levetiracetam, lorazepam, midazolam, N-desmethylclobazam, nordiazepam, oxycarbamezapine, perampanel, phenobarbital, phenytoin, pregabalin, rufinamide, stiripentol, topiramate, trazodone, vagus nerve stimulation, valproic acid, vigabatrin, and zonisamide.

10. The method of claim 1, wherein the dose of the CBD is increased to about 10 mg/kg/day.

11. The method of claim 1, wherein the dose of the CBD is increased to about 12 mg/kg/day.

12. The method of claim 1, wherein the dose of the CBD is increased to about 14 mg/kg/day.

13. The method of claim 1, wherein the dose of the CBD is increased to about 15 mg/kg/day.

14. The method of claim 1, wherein the dose of the CBD is increased to about 18 mg/kg/day.

15. The method of claim 1, wherein the dose of the CBD is increased to about 20 mg/kg/day.

16. A method of treating focal seizures in Lennox-Gastaut Syndrome or Tuberous Sclerosis Complex, comprising administering to a subject in need thereof a drug product comprising a cannabidiol (CBD) drug substance, wherein the CBD drug substance has a purity of at least 98% (w/w), and the CBD is administered at a dose of 5 mg/kg/day, and then the dose is increased by 2 to 5 mg/kg increments, up to 25 mg/kg/day.

17. The method of claim 16, wherein the focal seizures are focal seizures with impairment.

18. The method of claim 16, wherein the Lennox-Gastaut Syndrome or Tuberous Sclerosis Complex is treatment-resistant.

19. The method of claim 16, wherein the CBD comprises Δ9-tetrahydrocannabinol (THC).

20. The method of claim 19, wherein the CBD comprises not more than 0.15% (w/w) Δ9-tetrahydrocannabinol (THC).

21. The method of claim 16, wherein the dose of the CBD is increased to about 10 mg/kg/day.

22. The method of claim 16, wherein the dose of the CBD is increased to about 12 mg/kg/day.

23. The method of claim 16, wherein the dose of the CBD is increased to about 14 mg/kg/day.

24. The method of claim 16, wherein the dose of the CBD is increased to about 15 mg/kg/day.

25. The method of claim 16, wherein the dose of the CBD is increased to about 18 mg/kg/day.

26. The method of claim 16, wherein the dose of the CBD is increased to about 20 mg/kg/day.

27. The method of claim 16, wherein the CBD is administered in combination with one or more concomitant anti-epileptic drugs (AED).

28. The method of claim 27, wherein the one or more AED is selected from the group consisting of: carbamezapine, clobazam, clonazepam, clonidine, clorazepate, desmethylclobazam, diazepam, ethosuximide, felbamate, ketogenic diet, lacosamide, lamotrigine, levetiracetam, lorazepam, midazolam, N-desmethylclobazam, nordiazepam, oxycarbamezapine, perampanel, phenobarbital, phenytoin, pregabalin, rufinamide, stiripentol, topiramate, trazodone, vagus nerve stimulation, valproic acid, vigabatrin, and zonisamide.

* * * * *

UNITED STATES PATENT AND TRADEMARK OFFICE
CERTIFICATE OF CORRECTION

PATENT NO. : 12,064,399 B2  
APPLICATION NO. : 17/744224  
DATED : August 20, 2024  
INVENTOR(S) : Geoffrey Guy et al.

Page 1 of 1

It is certified that error appears in the above-identified patent and that said Letters Patent is hereby corrected as shown below:

In the Claims

Column 17, Line 30:
"*Cannabis*"
Should read:
-- Cannabis --

Signed and Sealed this  
Fourth Day of February, 2025

Coke Morgan Stewart  
*Acting Director of the United States Patent and Trademark Office*